United States Patent
Kikelj et al.

[11] Patent Number: 5,824,652
[45] Date of Patent: Oct. 20, 1998

[54] HETEROCYCLIC ACYLDIPEPTIDES, PROCESSES FOR THE PREPARATION THEREOF AND PHARMACEUTICAL COMPOSITIONS CONTAINING THE SAME

[75] Inventors: Danijel Kikelj; Elizabeta Suhadolc, both of Ljubljana; Alenka Rutar, Radlje ob Dravi; Slavko Pecar, Domzale; Alesa Puncuh, Kostanjevica ob Krki; Uros Urleb, Ljubljana; Vesna Leskovsek, Velenje; Gasper Marc, Vipava; Marija Sollner, Borovnica; Ales Krbavcic; Gregor Sersa, both of Ljubljana; Srdjan Novakovic, Grosuplje; Lucka Povsic; Anton Stalc, both of Ljubljana, all of Slovenia

[73] Assignees: Univerza v Ljubljani, Fakulteta za naravoslovje in technologijo, Oddelek za farmacijo; LEK, tovarna farmacevtskih in kemicnih izdelkov, d.d., both of Ljubljana, Slovenia

[21] Appl. No.: 537,782
[22] PCT Filed: Apr. 21, 1994
[86] PCT No.: PCT/SI94/00003
§ 371 Date: Jan. 4, 1996
§ 102(e) Date: Jan. 4, 1996
[87] PCT Pub. No.: WO94/24152
PCT Pub. Date: Oct. 27, 1994

[30] Foreign Application Priority Data

Apr. 22, 1993 [SI] Slovenia .............................. P-9300212

[51] Int. Cl.$^6$ .......................... A61K 38/00; C07D 471/02
[52] U.S. Cl. ........................... 514/19; 514/307; 546/113; 546/114; 546/115; 546/116; 560/39; 562/563; 562/575
[58] Field of Search ..................... 514/19, 307; 562/563, 562/575; 560/39; 546/113, 114, 115, 116

[56] References Cited

U.S. PATENT DOCUMENTS 5,321,216  6/1994  Pecar et al. .............................. 560/39

FOREIGN PATENT DOCUMENTS 0477912  4/1992  European Pat. Off. .

OTHER PUBLICATIONS

Goodman & Cilman's "The Pharmacological Basis of Therapeutics" 6th Ed. (MacMillan Publishing 1980) pp. 1249–1255.
Hasegawa et al. Chemical Abstract No. 93:239878z.

*Primary Examiner*—Cecilia J. Tsang
*Assistant Examiner*—Bennett Celsa
*Attorney, Agent, or Firm*—Pollock, Vande Sande & Priddy

[57] ABSTRACT

Heterocyclic acyldipeptides of the formula I

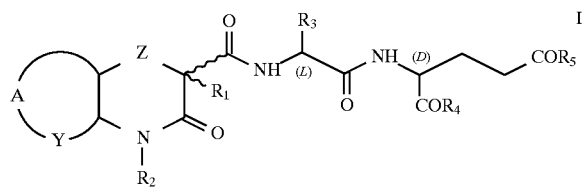

wherein
Z represents an oxygen or sulphur atom or a —$CH_2$- group;
$R_1$, $R_2$ and $R_3$ individually represent hydrogen or certain organic groups;
$R_4$ and $R_5$, which are identical or different, represent an $OR_6$ or $NHR_6$ group, wherein $R_6$ is hydrogen or certain organic groups;
Y represents a —$CH_2$—, =CH— or =N— group;
A represents a —$(CH_2)_3$— group when Y is —$CH_2$—, the two rings being transcondensed, or a

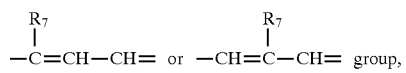

wherein $R_7$ represents H, F, Br, Cl, nitro, or certain organic groups when Y is =CH— or =N—; and their pharmaceutically acceptable salts are provided. These heterocyclic acyldipeptides and their salts are useful as active compounds in medicaments having immunostimulatory and antitumor activity.

19 Claims, 1 Drawing Sheet

HETEROCYCLIC ACYLDIPEPTIDES, PROCESSES FOR THE PREPARATION THEREOF AND PHARMACEUTICAL COMPOSITIONS CONTAINING THE SAME

This Application is a 371 of PCT/SI94/00003 filed Apr. 21, 1994.

TECHNICAL FILED OF THE INVENTION (IPC C 07D)

The invention belongs to the field of pharmaceutical industry and concerns novel heterocyclic acyldipeptides, processes for the preparation thereof and pharmaceutical compositions containing the same. Novel peptides of the present invention possess an immunostimulatory and antiumor activity.

BACKGROUND OF THE INVENTION

There exists a continuing need for novel medicaments having strong immunostimulatory and antitumor activity and as few side effects as possible. Recently, peptides having biological activity have been acquiring increasing significance in this field, including also muramyl dipeptide derivatives and analogues.

Muramyl peptides [A. Adam and E. Lederer, in Med. Res. Rev. 4, 111 (1984); G. Baschang, in Tetrahedron 45, 6331 (1989)] are components of bacterial cell walls having therapeutically interesting effects upon the immunological system. N-Acetylmuramyl-L-alanyl-D-isoglutamine (muramyl dipeptide, MDP) is the smallest essential structural element of bacterial cell wall having retained immunomodulatory activity. MDP has several undesired side effects such as pyrogenous and somnogenous activity, and it can also cause acute arthritis and anaphylactic reaction.

The synthesis of muramyl peptides is described in the articles by P. Lefrancier and E. Lederer, in Fortschr. Chemie Org. Naturstoffe 40, 1 (1981) and G. Baschang, in Tetrahedron 22, 6331 (1989).

Quite a few things are known about the relation between the structure of muramyl dipeptides and their activity [P. Lefrancier and E. Lederer, in Pure Appl. Chem. 59, 449 (1987)] and especially in the recent years it has become clear that the immunomodulatory activity of MDP analogues is not conditioned by an intact N-acetylmuramyl fragment. Muramyl dipeptide analogues having the N-acetylmuramyl moiety of the molecule derived or substituted by groups having preserved only some elements of the N-acetylmuramyl fragment are described e.g. in articles by I. Azuma et al., in Infect. Immun. 20, 600 (1987); T. Shiba et al., in Bull. Chem. Soc. Jpn. 51, 3307 (1978); M. Uemiya et al, in Infect. Immun. 24, 83 (1979); M. Inage et al., in Tetrahedron Lett. 21, 3767 (1980); K. Hemmi et al., in J. Am. Chem. Soc. 103, 7026 (1981); K. Hemmi et al., in Tetrahedron Lett. 23, 693 (1982); T. Gotoh et al., in J. Antibiot. 35, 1280 (1982); F. Floc'h et al., in Drugs of the Future 9, 763 (1984); G. H. Werner et al., in Experientia 42, 521 (1986); J. Danklmeier et al., in Liebigs Ann. Chem. 1990, 145; A. Hasegawa et al., in Gifu Daigaku Nogakubu Kenkyu Hokoku 42, 169 (1979); L. Azuma et al., in Infect. Immun. 33, 834 (1981); D. H. R. Barton et al., in J. Org. Chem. 54, 3764 (1989) as well as in the patents DE 36 34 013, U.S. Pat. No. 5,231,216 and EP 477 912. In the U.S. Pat. No. 4,322,341 hetercrocyclic acytetrapeptides having immunomodulatory properties are disclosed.

The present invention concerns novel heterocyclic acyldipeptides of the formula I wherein Z represents an oxygen or sulphur atom or a —$CH_2$— group;

$R_1$ represent hydrogen, a straight or branched chain 1–4C alkyl, cycloalkyl, cycloalkylalkyl, trifluoromethyl or benzyl group;

$R_2$ represents hydrogen, a straight or branched chain 1–4C alkyl, cycloalkyl, alkylcycloalkyl, dialkylaminoalkyl, acylaminoalkyl or benzyl group;

$R_3$ represents hydrogen, a straight or branched chain 1–12C alkyl or tri-fluoromethyl group;

$R_4$ and $R_5$, which are identical or different, represent an $OR_6$ or $NHR_6$ group, wherein $R_6$ is hydrogen, a straight or branched chain 1–18C alkyl or benzyl group;

Y represents a —$CH_2$—, =CH— or =N— group;

A represents a —$(CH_2)_3$— group when Y is —$CH_2$—, the two rings being transcondensed, or a $$-\overset{R_7}{\underset{|}{C}}=CH-CH= \quad \text{or} \quad -CH=\overset{R_7}{\underset{|}{C}}-CH=$$

group, wherein $R_7$ represents H, F, Br, Cl, a straight or branched chain 1–4C alkyl, 1–4C alkoxy, trifluoromethyl, nitro, amino, alkylamino or dialkylamino group, when Y is =CH— or =N—;

optically pure diastereomers of the compounds of formula I, pharmaceutically acceptable salts of the compounds of formula I and of optically pure diastereomers thereof having immunostimulatory and antitumor activity as well as pharmaceutical compositions containing the same.

The present invention is also is also concerned with an economical process for the preparation of heterocyclic acyldipeptides of formula I.

BEST AND VARIOUS MODES FOR CARRYING OUT INVENTION

The heterocyclic acyldipeptides of formula I are rigid analogues of carbocyclic MDP analogues described in U.S. Pat. No. 5,231,216. Therein, the acetamide group and the lactic acid fragment are part of the morpholine ring, while the fused cyclohexane, substituted benzene or pyridine ring imitate the tetrahydropyrane ring of D-glucosamine.

Novel heterocyclic acyldipeptides of formula I are prepared by reacting heterocyclic carboxylic acids of formula II wherein Z, A, Y, $R_1$ and $R_2$ have the same meaning as in formula I, with dipeptides of formula III

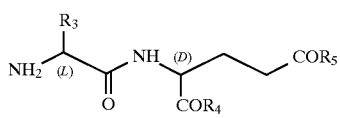

wherein $R_3$, $R_4$ and $R_5$ have the same meaning as in formula I. When $R_4$ and/or $R_5$ are benzyl, they can have the meaning of a protecting group, which can be removed by hydrogenation. The hydrogenation is carried out at normal pressure and at room temperature in polar solvents such as acetic acid or lower alcohols such as methanol or in tetrahydrofuran. Pd/C is used as the catalyst.

The reaction of heterocyclic carboxylic acids of formula II with dipeptides of formula III to heterocyclic acyldipeptides of formula I is carried out in polar aprotic solvents such as N,N-dimethylformamide, tetrahydrofuran or 1,4-dioxan at temperatures from −10° to 25° C., using common reagents for the formation of the peptide bond such as diphenyl phosphoryl azide, chloroformates or dicyclohexylcarbodiimide.

Dipeptides of formula III are either known and described in the literature [e.g. E. Lefrancier et al., in Bull. Soc. Chim. Biol. 49, 1257 (1969); S. Kusumoto et al., in Bull. Chem. Soc. Jpn. 49, 533 (1976)] or can be prepared by known analogous methods using protecting groups and reagents for the formation of the peptide bond that are commonly known in peptide chemistry [M. Bodanszky and A. Bodanszky, The Practice of Peptide Synthesis, Springer, Berlin, Heidelberg, New York, Tokyo (1986)].

The compounds of formula I are obtained as mixtures of diastereomers, which in some cases can be separated by column chromatography on silica gel or other common supports.

The starting heterocyclic carboxylic acids of formula II, wherein Y represents a —CH= or =N— group and Z represents an oxygen or sulphur atom or a —CH$_2$— group are known compounds described in the literature. The preparation thereof is described in the article by H. Techer et al., in C. R. Acad. Sc. Paris C269,154 (1969), in YU application P-2092/90, in EP 382 687 and in the article by D. Kikelj et al., in J. Heterocyclic Chem. 30,597 (1993). Alternatively, they can be prepared from the corresponding esters, whose synthesis is described in FR 2,024,816, by alkaline hydrolysis according to commonly known methods. The hydrolysis of the esters is carried out at room temperature with an aqueous solution of alkali hydroxides in polar organic solvents such as methanol, ethanol, dioxan or tetrahydrofuran.

The starting carboxylic acids of formula II, wherein Y represents a —CH$_2$— group and Z represents an oxygen atom, are prepared according to the following reaction scheme

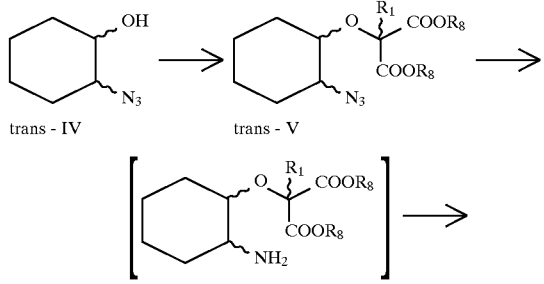

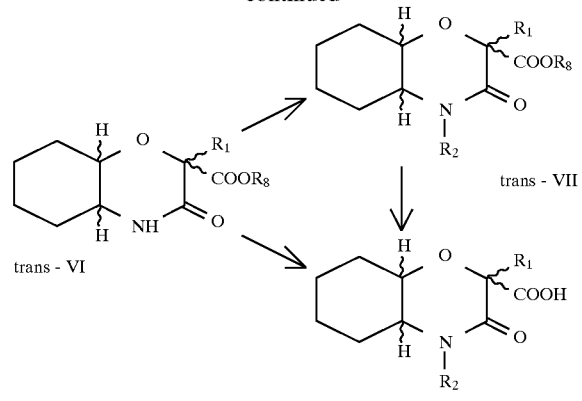

by reacting trans-2-azidocyclohexanol IV [G. Swift and D. Swern, in J. Org. Chem. 32, 511(1967)] with dialkyl-2-halomalonates of formula VIII

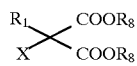            VIII wherein $R_1$ has the same meaning as in formula I, $R_8$ is a straight or branched chain 1–4C alkyl group and X represents a bromine or chlorine atom, to 2-substituted trans-dialkyl-2-(2'-azidocyclohexyloxy)malonates of formula V, wherein $R_1$ and $R_8$ have the same meaning as in formula VIII. The reaction of trans-2-azidocyclohexanol of formula IV with dialkyl malonates of formula VIII to compounds of formula V is carried out in polar aprotic solvents such as tetrahydrofuran or 1,4dioxan, in the presence of a base such as NaH of NaNH$_2$ and at temperatures from 20° to 100° C.

The compounds of formula V are, by the reduction of the azide group according to commonly known methods, followed by spontaneous cyclization, converted to 2-unsubstituted or 2-substituted trans-2-alkoxycarbonyloctahydro-2H-1,4benzoxazine-3-ones of formula VI. The reduction is carried out with e.g. SnCl$_2$ or by hydrogenolysis in the presence of Pd/C catalyst in polar solvents such as lower alcohols.

The compounds of formula VI are alkylated according to commonly known methods by the reaction thereof with alkyl halides of formula IX

R$_2$X            IX wherein $R_2$ has the same meaning as in formula I and X is a bromine or iodine atom, in the presence of a base such as NaH, NaNH$_2$ or potassium tert-butoxide, in anhydrous inert organic solvents such as benzene, toluene or xylene, at a temperature up to the reflux temperature or under phase transfer catalysis conditions.

The esters of formula VI are, by alkaline hydrolysis e.g. with an aqueous solution of an alkali hydroxide in 1,4-dioxan, tetrahydrofuran or lower alcohol at room temperature, converted to carboxylic acids of formula II.

The esters of formula V can also be prepared, as shown in the following scheme

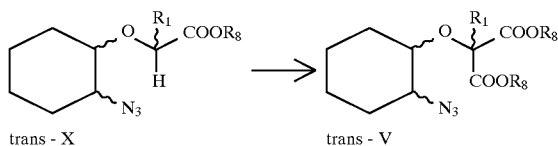

trans - X    trans - V by reacting trans-alkyl-2-(2'-azidocyclohexyloxy) carboxylates of formula X, whose preparation is described in the articles by D. Kikelj et al., in Synth. Commun. 19, 2665 (1989) and D. Kikelj et al., in Monatsh. Chem. 122, 275 (1991), with chloroformates of formula XI ClCOOR$_8$    XI or dialkylcarbonates of formula XII

CO(OR$_8$)$_2$    XI in the presence of lithium diisopropylamide in tetrahydrofuran in accordance with a similar process as described by H. Griengl et al., in Monatsh. C hem. 118, 415 (1987).

The invention also concerns optically pure diastereomers of compounds of formula I, which are prepared from enantiomers or diastereomers of heterocyclic carboxylic acids of formula II by reacting the latter with dipeptides of formula III as described above.

The enantiomers of heterocyclic carboxylic acids of formula II, wherein Y represents a =CH— or =N— group and Z represents an oxygen or sulphur atom or a —CH$_2$— group, can be obtained by the resolution of the racemic mixture of heterocyclic carboxylic acids of formula II using the commonly known methods for the resolution of carboxylic acids, which are described e.g. in J. Jacques, A. Collet and S. H. Wilen, Enantiomers, Racemates and Resolution, John Wiley & Sons, New York, Chichester, Brisbane, Toronto (1981).

Pure diastereomers of compounds of formula II, wherein Y represents a —CH$_2$— group and Z represents an oxygen atom, can be obtained by the resolution of a mixture of (2R/S,4aR,8aR)-II or (2R/S,4aS,8aS)-II, which can be prepared from (1R,2R)-2-azidocyclohexanol and (1S,2S)-2-azidocyclohexanol, respectively, as described above for the preparation of the diastereomeric mixture of formula II from rac-trans-2-azidocyclohexanol.

(1R,2R)-2-azidocyclohexanol and (1S,2S)-2-azidocyclohexanol are known compounds, which are described in the literature. The preparation thereof is described in the articles by Hoenig et al., in Tetrahedron Lett. 29, 1903 (1988) and H. Hoenig et al., in J. Chem. Soc. Perkin Trans I 1989, 2341.

The invention is illustrated by the following non-limiting Examples

EXAMPLE 1 trans-Diethyl-2-(2'-azidocyclohexyloxy)-2-methylmalonate

To a suspension of NaH (1.8 g, 75 mmoles) in anhydrous dioxan (75 ml) in a three-neck bottle equipped with a reflux water-cooled condenser and magnetic stirrer, trans-2-azidocyclohexanol (10.6 g, 75 mmoles) was added dropwise at 70° C. The reaction mixture was stirred at 70° C. for 1.5 hours, followed by a dropwise addition of diethyl-2-bromo-2-methylmalonate (19 g, 75 mmoles). The reaction mixture was stirred at a temperature of 70°–80° C. for 4 hours. The solvent was evaported, followed by addition of water (200 ml) and extraction with ethyl acetate (5×50 ml). The organic phases were combined, dried over MgSO$_4$, filtered and the solvent was evaporated. The product was distilled in vacuo and the fraction, which distilled over between 120° and 150° C./0.20–0.67 mbar, was further purified by column chromatography (silicagel; chloroform/methanol=100:1). Thus there were obtained 6.72 g (27%) of a pale yellow, viscous liquid.

IR (film): ν=2980, 2940, 2860, 2110, 1740, 1450, 1375, 1270, 1150, 1115, 1060, 1025, 860 cm$^{-1}$.

$^1$H-NMR (300 MHz, CDCl$_3$): δ=1.289 (1.287) (t, 6H, J=7.1 Hz, CH$_2$CH$_3$), 120–1.50 (m, 4H, 4H$_{ax}$), 1.68 (s, 3H, CH$_3$), 1.6–2.20 (m, 4H, 4H$_{eq}$), 3.36–3.48 (m, 1H, CH), 3.54–3.68 (m, 1H, CH), 4.25 (4.24) (q, 4H, J=7.1 Hz, CH$_2$CH$_3$) ppm.

Analysis for C$_{14}$H$_{23}$N$_3$O$_5$ (313.35): calc.: 53.66% C 7.40% H 13.41% N found: 53.32% C 7.36% H 13.49% N

EXAMPLE 2 trans-Ethyl-2-(2'-azidocyclohexyloxy)-acetate

A solution of trans-2-(2'-azidocyclohexyloxy)-acetic acid (11.16 g, 56 mmoles) and concentrated sulphuric acid (0.8 ml) in anhydrous ethanol (30 ml) was heated for 3 hours at reflux temperature, then the mixture was poured into ice water (150 ml) and extracted with n-hexane (4×60 ml). The combined hexane phases were dried over MgSO$_4$, filtered and the solvent was evaporated. The crude product was distilled in vacuo (boiling point: 129° C./0.67 mbar), yielding 8.6 g (68%) of the title compound in the form of a yellow oil.

IR (film): ν=2940, 2860, 2100, 1755, 1730, 1450, 1385, 1265, 1200, 1150, 1125, 1030, 975, 915, 850 cm$^{-1}$.

$^1$H-NMR (300 MHz, CDCl$_3$): δ=1.29 (t, 3H, J=7.1 Hz, CH$_3$), 1.19–1.41 (m, 4H, 4H$_{ax}$), 1.66–1.78 (m, 2H, 2H$_{eq}$), 1.96–2.19 (m, 2H, 2H$_{eq}$), 3.16–3.26 (m, 1H, 2'-H), 3.33–3.42 (m, 1H, 1'-H), 4.23 (q, 2H, J=7.1 Hz, CH$_2$), 4.24 (s, 2H, OCH$_2$) ppm.

Analysis for C$_{10}$H$_{17}$N$_3$O$_3$ (313.35): calc.: 52.85% C 7.54% H 18.49% N found: 52.52% C 7.52% H 18.67% N

EXAMPLE 3 trans-Diethyl-2-(2'-azidocyclohexyloxy)-malonate

To a solution of lithium diisopropylamide (2.14 g, 20 mmoles) in anhydrous tetrahydrofuran (20 ml), ethyl-2-(2'-azidocyclohexyloxy)acetate (3.4 g, 15 mmoles) was added at −90° C. with stirring, followed by the addition of ethylchloroformate (1.63 g, 15 mmoles). After stirring for 1 hour at −90° C., the temperature was allowed to rise to −50° C.; 6N HCl (3 ml) was added and the mixture was extracted with ether. The combined etheral phases were washed with a saturated NaHCO$_3$ solution, dried over MgSO$_4$, filtered and the solvent was distilled off in vacuo. Thus there were obtained 2.45 g (60%) of the title compound in the form of a yellow oil, which was purified by distillation in vacuo.

IR (film): ν=2938, 2864, 2098, 1756, 1693, 1604, 1451, 1370, 1263, 1202, 1150, 1124, 1030, 971, 909, 841, 663 cm$^{-1}$.

$^1$H-NMR (300 MHz, CDCl$_3$): δ=1.00–1.50 (m, 4H, 4H$_{ax}$), 1.29 (t, 6H, J=7.1 Hz, 2CH$_3$), 1.60–1.80 (m, 2H, 2H$_{eq}$), 1.80–2.15 (m, 1H, 1H$_{eq}$), 2.20–2.40 (m, 1H, 1H$_{eq}$), 3.15–3.28 (m, 1H, 2'-H), 3.30–3.45 (m, 1H, 1'-H), 4.23 (q, 4H, J=7.1 Hz, 2CH$_2$), 4.24 (s, 1H, CH) ppm.

EXAMPLE 4 trans-Ethyl-2-methyl-3-oxo-octahydro-2H-1,4-benzoxazie-2-carboxylate

To a solution of SnCl$_2$.2H$_2$O (4.06 g, 18 mmoles) in methanol (12 ml), a solution of trans-diethyl-2-(2'- azidocyclohexyloxy)-2-methylmalonate (3.76 g, 12 mmoles) in methanol (12 ml) was added dropwise with stirring on an ice bath. The mixture was stirred at room temperature overnight, the solvent was evaporated and the residue was stirred for 15 minutes with a saturated $Na_2CO_3$ solution (75 ml). The mixture was extracted with ether (5×50 ml) and the combined organic phases were dried over $MgSO_4$. The solution was filtered, the solvent was evaporated an 1 the product was recrystallized from ethyl acetate. Thus there were obtained 1.88 g (65%) of the title product in the form of white crystals, m.p. 92°–94° C.

IR (KBr): ν=3190, 3080, 2980, 2940, 2880, 1740, 1670, 1465, 1450, 1420, 1380, 1360, 1340, 1240, 1130, 1080, 1020, 965, 865, 810, 780, 730 cm$^{-1}$.

$^1$H-NMR (300 MHz, CDCl$_3$): δ=1.29 (t, 3H, J=7 Hz, CH$_2$CH$_3$), 1.2–2.0 (m, 8H, 4CH$_2$), 1.68 (s, 3H, CH$_3$), 3.22–3.42 (m, 2H, 2CH), 4.23 (m, 2H, CH$_2$CH$_3$), 7.15 (s, br, 1H, NH) ppm.

$^1$C-NMR (75.44 MHz, CDCl$_3$): δ=13.87 (C-12), 20.21 (C-9), 23.23 (C-6/7), 24.13 (C-6/7), 29.74 (C-5/8), 30.33 (C-5/8), 55.76 (C-4a), 61.91 (C-11), 75.07 (C-8a), 81.46 (C-2), 169.11 (C-10), 169.34 (C-3) ppm.

MS (70 eV, 100° C.): calc.: 241.29 found: 241 (M$^+$)

Analysis for C$_{12}$H$_{19}$NO$_4$ (241.287): calc.: 59.73% C 7.94% H 5.81% N found: 59.88% C 8.12% H 5.80% N

EXAMPLE 5 trans-2-Methyl-3-oxo-octahydro-2H-1,4-benzoxazine-2-carboxylic acid

A solution of trans-ethyl-2-methyl-3-oxo-octahydro-2H-1,4-benzoxazine-2-carboxylate (4.80 g, 19.8 mmoles) and 1N NaOH (29,7 ml, 20.7 mmoles) in dioxan (80 ml) was stirred for 20 hours. The solvent was evaporated, 1N HCl (90 ml, 90 mmoles) was added to the residue and the mixture was extracted with ethyl acetate (4×60 ml). The organic phase was dried over MgSO$_4$, the solvent was evaporated and the product was recrystallized from ethyl acetate. Thus there were obtained 2.3 g (54,5%) of the title product in the form of white crystals, m.p. 142°–144° C.

IR (KBr): ν=3280, 2940, 2870, 2500, 1930, 1730, 1630, 1460, 1450, 1420, 1380, 1350, 1315, 1300, 1275, 1180, 1165, 1150, 1115, 1080, 970, 930, 880, 850, 810, 760, 710 cm$^{-1}$.

$^1$H-NMR (300 MHz, CDCl$_3$): δ=1.20–2.15 (m, 8H, 4CH$_2$), 1.70 (1.68) (s, 3H, CH$_3$), 3.10–3.15 (3.15–3.20) (m, 1H, H-4a/8a), 3.50–3.62 (3.40–3.50) (m, 1H, H-4a/8a), 171.75 (7.70) (s, br, 1H, NH), 11.2 (s, br, 1H, COOH) ppm.

$^{13}$C-NMR (75.44 MHz, CDCl$_3$): δ=21.56 (C-9), 23.36 (C-6/7), 24.00 (C-6/7), 29.60 (C-5/8), 30.22 (C-5/8), 56.40 (C-4a), 75.87 (C-8a), 80.11 (C-2), 171.26 (C-10), 171.75 (C-3) ppm.

MS (70 eV, 80° C.): calc.: 213.23 found: 213 (M$^+$)

Analysis for C$_{10}$H$_{15}$NO$_4$ (213.233): calc.: 56.53% C 7.09% H 6.57% N found: 56.24% C 7.21% H 6.27% N

EXAMPLE 6 trans-Ethyl-2,4-dimethyl-3-oxo-octahydro-2H-1,4-benzoxazine-2-carboxylate

To a solution of trans-ethyl-2-methyl-3-oxo-octahydro-2H-1,4-benzoxazine-2-carboxylate (483 mg, 2 mmoles) in anhydrous toluene (10 ml), NaH (96 mg, 4 mmoles) and methyl iodide (710 mg, 5 mmoles) were added and the mixture was heated for 30 minutes at reflux temperature. After the completion of the reaction, the toluene solution was washed with 1N HCl (10 ml), 1N NaOH (10 ml) and a saturated NaCl solution (10 ml). The solution was dried over MgSO$_4$ and the solvent was evaporated. Thus there were obtained 319 mg (62%) of a yellow product, which was purified by column chromatography (silica gel; chloroform/methanol=9:1). Thus there were obtained 246 mg (48%) of the title compound in the form of a viscous oil.

IR (film): ν=3490, 2940, 2867, 1478, 1660, 1454, 1374, 1311, 1269, 1147, 1090, 1021, 866, 745, 698, 590, 524 cm$^{-1}$.

$^1$H-NMR (300 MHz, CDCl$_3$): δ=1.20 (t, 3H, J=7.1 Hz, CH$_2$CH$_3$), 1.00–1.48 (m, 4H, 4H$_{ax}$), 1.62 (s, 3H, CH$_3$), 1.70–1.83 (m, 2H, 2H$_{eq}$), 1.85–1.98 (m, 1H, 1H$_{eq}$), 2.10–2.20 (m, 1H, 1H$_{eq}$), 2.89 (s, 3H, N—$_3$), 3.18–3.32 (m, 1H, CH), 3.36–3.48 (m, CH1H, CH), 4.15 (4.22) (q, 2H, J=7.1 Hz, CH$_2$CH$_3$) ppm.

Analysis for C$_{13}$H$_{21}$NO$_4$ (255.307): calc.: 61.15% C 8.29% H 5.49% N found: 61.10% C 8.63% H 5.37% N

EXAMPLE 7 trans-2,4-Dimethyl-3-oxo-octahydro-2H-1,4-benzoxazine-2-carboxylic acid trans-Ethyl-2,4-dimethyl-3-oxo-octahydro-2H-1,4-benzoxazine-2-carboxylate (180 mg, 0.71 mmoles) and 1N NaOH (1.1 ml, 1.1 mmoles) in dioxan (5 ml) were stirred for 20 hours. The solvent was evaporated, 1N HCl (11 ml, 11 mmoles) was added to the residue and the mixture was extracted with ethyl acetate (3×20 ml). The organic phase was dried over MgSO$_4$ and the solvent was evaporated. Thus there were obtained 114 mg (71%) of the title product in the form of a viscous yellow oil.

IR (film): ν=3707–3272, 2941, 2867, 1746, 1634, 1452, 1376, 1293, 1256, 1197, 1147, 1089, 872, 682, 586, 487 cm$^{-1}$.

$^1$H-NMR (300 MHz, CDCl$_3$): δ=1.02–1.56 (m, 4H, 4H$_{ax}$), 1.69 (s, 3H, CH$_3$), 1.56–2.25 (3m, 4H, 4H$_{eq}$), 2.92 (s, 3H, N—CH$_3$), 3.14–3.32 (m, 1H, CH), 3.35–3.56 (m, 1H, CH), 9.35 (s, br, 1H, COOH) ppm.

EXAMPLE 8

(+)-1-Phenylethylammonium 3,4-dihydro-2-methyl-3-oxo-2H-1,4-benzoxazine-2 -carboxylate 3,4-Dihydro-2-methyl-3-oxo-2H-1,4-benzoxazine-2-carboxylic acid (6.00 g, 29 mmoles) was dissolved in absolute ethanol (250 ml) and S-(−)-1-phenylethylamine (3.51 g, 29 mmoles) was added to this solution. After the addition of the optically pure amine, the separation of a white precipitate set in. After stirring for half an hour at room temperature, this precipitate was filtered off. The salt was recrystallized from absolute ethanol. Thus there were obtained 4.17 g of the title product in the form of white crystals, m.p. 180°–183° C.

Yield: 85%

Specific rotation: $[α]^{20}_D$=+50.8° (c=0.5, methanol)

IR (KBr): ν=3210, 3160, 3100, 3000, 2520, 1700, 1630, 1505, 1450, 1345, 1235, 1125, 950, 930, 830, 755, 700 cm$^{-1}$.

$^1$H-NMR (300 MHz, DMSO-d$_6$): δ=1.36 (d, 3H, J=6.8 Hz, CH$_3$-phenylethylamine), 1.53 (s, 3H, CH$_3$), 4.21 (q, 1H, J=6.7 Hz, CH-phenylethylamine), 6.75–6.88 (m, 4H, 4H-arom.), 7.31–7.43 (m, 5H, 5H-arom. (phenyl)), 8.69 (s-broad, 3H, —NH$_3$), 10.28 (s, 1H, NH) ppm.

Analysis for C$_{18}$H$_{20}$N$_2$O$_4$ (328.36): calc.: 65.84% C 6.14% H 8.53% N found: 64.99% C 5.97% H 8.60% N

EXAMPLE 9

(−)-1-Phenylethylammonium 3,4dihydro-2-methyl-3-oxo-2H-1,4-benzoxazine-2-carboxylate 3,4-Dihydro-2-methyl-3-oxo-2H-1,4-benzoxazine-2-carboxylic acid (7.00 g, 33.9 mmoles) was dissolved in absolute ethanol (290 ml) and R-(+)-1-phenylethylamine (4.11 g, 33.9 mmoles) was added to this solution. After the addition of the optically pure amine, the separation of a white precipitate set in. After stirring for half an hour at room temperature, this precipitate was filtered off. The salt was recrystallized from absolute ethanol. Thus there were obtained 5.00 g of the title product in the form of white crystals, m.p. 177°–178° C.

Yield: 86%

Specific rotation: $[\alpha]^{20}_D = -50.2°$ (c=0.5, methanol)

IR (KBr): ν=3205, 3158, 3090, 2987, 1701, 1625, 1563, 1501, 1449, 1400, 1343, 1231, 1124, 757, 701, 669, 576, 533 cm$^{-1}$.

$^1$H-NMR (250.13 MHz, DMSO-d$_6$): δ=1.40 (d, 3H, J=6.8 Hz, CH$_3$-phenylethylamine), 1.50 (s, 3H, CH$_3$), 4.25 (q, 1H, J=6.8 Hz, CH-phenylethylamine), 6.70–6.90 (m, 4H, 4H-arom.), 7.30–7.50 (m, 5H, 5H-arom. (phenyl)), 8.69 (s-broad, 3H, —NH$_3$), 10.12 (s, 1H, NH) ppm.

Analysis for C$_{18}$H$_{20}$N$_2$O$_4$ (328.36): calc.: 65.84% C 6.14% H 8.53% N found: 66.00% C 5.97% H 8.71% N

EXAMPLE 10

(−)-1-Phenylethylammonium 3,4-dihydro 2,4-dimethyl-3-oxo-2H-1,4-benzoxazine-2-carboxylate 3,4-Dihydro-2,4-dimethyl-3-oxo-2H-1,4-benzoxazine-2-carboxylic acid (1.00 g, 4.5 mmoles) was dissolved in absolute ethanol (12 ml) and S-(−)-1-phenylethylamine (0.55 g, 4.5 mmoles) was added to this solution. Only after a few hours the separation of a white precipitate set in. The salt was filtered off and recrystallized from absolute ethanol. Thus there were obtained 0.37 g of the title product in the form of white crystals, m.p. 210°–211° C.

Yield: 48%

Specific rotation: $[\alpha]^{20}_D = -79.0°$ (c=0.5, methanol)

IR (KBr): ν=3022, 1694, 1636, 1500, 1397, 1358, 1281, 1240, 1135, 1039, 854, 777 cm$^{-1}$.

Analysis for C$_{19}$H$_{22}$N$_2$O$_4$ (342.18):
calc.: 66.64% C 6.48% H 8.18% N
found: 66.59% C 6.50% H 8.22% N

EXAMPLE 11

(+)-1-Phenylethylammonium 3,4-dihydro-2,4-dimethyl-3-oxo-2H-1,4-benzoxazine-2-carboxylate 3,4-Dihydro-2,4-methyl-3-oxo-2H-1,4-benzoxazine-2-carboxylic acid (0.57 g, 2.6 mmoles), which was obtained by the acidification of the residue obtained by the evaporation of the mother liquor after the resolution of the N-methylated acid with S-(−)-phenyletyhlamine as described in Example 10, was dissolved in absolute ethanol (5 ml) and R-(+)-1-phenylethylamine (0.31 g, 2.6 mmoles) was added to this solution. After the addition of the optically pure amine, the separation of a white precipitate set in. After stirring for half an hour at room temperature, this precipitate was filtered off. The salt was recrystallized from absolute ethanol. Thus there were obtained 0.25 g of the title compound in the form of white crystals, m.p. 211°–213° C.

Yield: 16%

Specific rotation: $[\alpha]^{20}_D = +90.4°$ (c=0.5, methanol)

IR (KBr): ν=3022, 1694, 1636, 1500, 1397, 1358, 1281, 1240, 1135, 1039, 854, 777 cm$^{-1}$.

$^1$H-NMR (300 MHz, DMSO-d$_6$): δ=1.35 (d, 3H, J=6.8 Hz, CH$_3$-phenylethylamine), 1.55 (s, 3H, CH$_3$), 3.22 (s, 3H, N—CH$_3$), 4.19 (q, 1H, J=6.8 Hz, CH-phenylethylamine), 6.90–7.02 (m, 4H, 4H-arom.), 7.31–7.42 (m, 5H, 5H-arom. (phenyl)), 8.63 (s-broad, 3H, N—NH$_3$), 11.00 (s-broad, 1H, NH) ppm.

Analysis for C$_{19}$H$_{22}$N$_2$O$_4$ (342.18): calc.: 66.64% C 6.48% H 8.18% N found: 66.60% C 6.53% H 8.20% N

EXAMPLE 12

(S)-(+)-3,4Dihydro-2-methyl-3-oxo-2H-1,4-benzoxazine-2-carboxylic acid (+)-1-Phenylethylammonium 3,4-dihydro-2-methyl-3-oxo-2H-1,4-benzoxazine-2-carboxylate (4.17 g, 12.7 mmoles) was suspended in water (120 ml) and acidified with 1M HCl to pH=1. The precipitate (2.42 g), which separated, was filtered off, washed with water and recrystallized from a mixture of ethanol and hexane 1:3. The melting point of white crystals was 168°–172° C.

Yield: 92%

Specific rotation: $[\alpha]^{20}_D = +68.6°$ (c=0.5, methanol)

IR (KBr): ν=3299, 2920, 2596, 1756, 1660, 1610, 1501, 1424, 1380, 1257, 1132, 964, 892, 765 cm$^{-1}$.

$^1$H-NMR (250.13 MHz, DMSO-d$_6$): δ=1.67 (s, 3H, CH$_3$), 6.82—7.00 (m, 4H, 4H-arom.), 10.80 (s-broad, 1H, NH) ppm.

Analysis for C$_{10}$H$_9$NO$_4$ (207.18): calc.: 57.97% C 4.38% H 6.76% N found: 58.04% C 4.56% H 6.47% N

EXAMPLE 13

(R)-(−)-3,4-Dihydro-2-methyl-3-oxo-2H-1,4-benzoxazine-2-carboxylic acid

This compound was prepared from (−)-1-phenylethylammonium 3,4-dihydro-2-methyl-3-oxo-2H-1,4-benzoxazine-2-carboxylate according to the procedure described in Example 12. The title product was in the form of white crystals, m.p. 168°–171° C.

Yield: 90%

Specific rotation $[\alpha]^{20}_D = -68.7°$ (c=0.5, methanol)

IR (KBr): ν=3310, 2610, 2360, 1750, 1670, 1615, 1505, 1430, 1380, 1260, 1230, 970, 765, 670, 640, 575, 450 cm$^{-1}$.

$^1$H-NMR (250.13 MHz, DMSO-d$_6$): δ=1.67 (s, 3H, CH$_3$), 6.84–7.04 (m, 4H, 4H-arom.), 10.80 (s-broad, 1H, NH) ppm.

Analysis for C$_{10}$H$_9$NO$_4$ (207.18): calc.: 57.97% C 4.38% H 6.76% N found 58.00% C 4.25% H 6.75% N

EXAMPLE 14

(S)-(+)-Methyl-3,4-dihydro-2-methyl-3-oxo-2H-1,4-benzoxazine-2-carboxylate

To a solution of (+)-3,4-dihydro-2-methyl-3-oxo-2H-1,4-benzoxazine-2-carboxylic acid (1.95 g, 9.4 mmoles) in anhydrous methanol (20 ml), concentrated sulphuric acid (0.2 ml) was added and the reaction mixture was heated for 3 hours at reflux temperature. The solvent was then evaporated, the obtained crystals were washed with ice-cold water and filtered off. The title product was in the form of white crystals, m.p. 151°–153° C.

Yield: 92%

Specific rotation: $[\alpha]^{20}_D=+44.5°$ (c=0.5, methanol)

IR (KBr): ν=3219, 1758, 1691, 1610, 1500, 1434, 1376, 1251, 1126, 975, 760 cm$^{-1}$.

$^1$H-NMR (300 MHz, DMSO-d$_6$): δ=1.70 (s, 3H, CH$_3$), 3.64 (s, 3H, —OCH$_3$), 6.72–7.04 (m, 4H, 4H-arom.), 10.97 (s, 1H, NH) ppm.

Analysis for C$_{11}$H$_{11}$NO$_4$ (221.21): calc.: 59.73% C 5.01% H 6.33% N found: 59.56% C 4.89% H 5.94% N

EXAMPLE 15

(R)-(−)-Methyl-3,4-dihydro-2-methyl-3-oxo-2H-1,4-benzoxazine-2-carboxylate

This compound was prepared from (−)-3,4-dihydro-2-methyl-3-oxo-2H-1,4-benzoxazine-2-carboxylic acid according to the procedure described in Example 14. The title product was in the form of white crystals, m.p. 153°–157° C.

Yield: 95%

Specific rotation: $[\alpha]^{20}_D=-43.6°$ (c=0.5, methanol)

IR (KBr): ν=3224, 1758, 1690, 1610, 1500, 1433, 1376, 1251, 1125, 975, 760 cm$^{-1}$.

$^1$H-NMR (300 MHz, DMSO-d$_6$): δ=1.70 (s, 3H, CH$_3$), 3.64 (s, 3H, N—OCH$_3$), 6.89–7.04 (m, 4H, 4H-arom.), 10.97 (s, 1H, NH) ppm.

Analysis for C$_{11}$H$_{11}$NO$_4$ (221.21): calc.: 59.73% C 5.01% H 6.33% N found: 59.32% C 4.85% H 5.96% N

EXAMPLE 16

(S)-(+)-Methyl-2,4dimethyl-3,4-dihydro-3-oxo-2H-1,4-benzoxazine-2-carboxylate

To a solution of (+)-methyl-3,4-dihydro-2-methyl-3-oxo-2H-1,4-benzoxazine-2-carboxylate (0.9 g, 4.1 mmoles) in anhydrous toluene (20 ml), NaH (0.12 g, 5.1 mmoles) and methyl iodide (0.87 g, 6.1 mmoles) were added with stirring and the mixture was heated at reflux temperature for 2 hours. After the completion of the reaction, the toluene solution was washed with water (2×20 ml), 0.1M HCl (2×20 ml) and saturated NaCl solution (20 ml). The solution was dried over MgSO$_4$ and the solvent was evaporated. Thus there were obtained 0.68 g of the title product, which was recrystallized from a mixture of hexane and diethyl ether. The title product was in the form of white crystals, m.p. 76°–78° C.

Yield: 71%

Specific rotation: $[\alpha]^{20}_D=+69.5°$ (c=0.5, methanol)

IR (KBr): ν=3448, 2959, 1735, 1686, 1504, 1440, 1385, 1282, 1245, 1125, 1043, 974, 750, 668, 509 cm$^{-1}$.

$^1$H-NMR (300 MHz, DMSO-d$_6$): δ=1.72 (s, 3H, CH$_3$), 3.33 (s, 3H, N—CH$_3$), 3.61 (s, 3H, —OCH$_3$), 7.06–7.20 (m, 4H, 4H-arom.) ppm.

Analysis for C$_{12}$H$_{13}$NO$_4$ (235.24): calc.: 61.27% C 5.57% H 5.95% N found: 61.50% C 5.94% H 5.62% N

EXAMPLE 17

(R)-(−)-Methyl-3,4-dihydro-2,4-dimethyl-3-oxo-2H-1,4-benzoxazine-2-carboxylate

This compound was prepared from (−)-methyl-3,4-dihydro-2-methyl-3-oxo-2H-1,4-benzoxazine-2-carboxylate according to the procedure described in Example 16. The title product was in the form of white crystals, m.p. 75°–78° C.

Yield: 71%

Specific rotation: $[\alpha]^{20}_D=-64.6°$ (c=0.5, methanol)

IR (KBr): ν=3448, 2960, 1735, 1685, 1503, 1440, 1387, 1282, 1245, 1124, 1043, 973, 749 cm$^{-1}$.

$^1$H-NMR (300 MHz, DMSO-d$_6$): δ=1.72 (s, 3H, CH$_3$), 3.32 (s, 3H, N—CH$_3$), 3.61 (s, 3H, —OCH$_3$), 7.05–7.21 (m, 4H, 4H-arom.) ppm.

Analysis for C$_{12}$H$_{13}$NO$_4$ (235.24): calc.: 61.27% C 5.57% H 5.95% N found: 61.19% C 5.19% H 5.73% N

EXAMPLE 18

(S)-(+)-3,4-Dihydro-2,4-dimethyl-3-oxo-2H-1,4-benzoxazine-2-carboxylic acid

A) (S)-(+)-Methyl-3,4-dihydro-2,4-dimethyl-3-oxo-2H-1,4-benzoxazine-2-carboxylate (0.58 g, 2.5 mmoles) was dissolved in dioxan (15 ml), 1M NaOH (3 ml, 3 mmoles) was added thereto and the mixture was stirred at room temperature for 24 hours.

The solvent was evaporated and the residue was dissolved in water (15 ml). The aqueous phase was acidified with 1M HCl under the separation of a precipitate, which was recrystallized from a mixture of hexane and ethanol. The title product was in the form of white crystals (0.47 g), m.p. 139°–143° C.

Yield: 88%

Specific rotation: $[\alpha]^{20}_D=+89.5°$ (c=0.5, methanol)

IR (KBr): ν=3416, 1972, 1678, 1608, 1502, 1449, 1390, 1273, 1155, 1038, 850, 761 cm$^{-1}$.

$^1$H-NMR (300 MHz, DMSO-d$_6$): δ=1.70 (s, 3H, CH$_3$), 3.31 (s, 3H, N—CH$_3$), 7.02–7.19 (m, 4H, 4H-arom.) ppm.

Analysis for C$_{11}$H$_{11}$NO$_4$ (221.21): calc.: 59.73% C 5.01% H 6.33% N found: 59.83% C 4.89% H 6.56% N B) Alternatively, this compound was prepared from (+)-1-phenylethyl-ammonium 3,4-dihydro-2,4-dimethyl-3-oxo-2H-1,4-benzoxazine-2-carboxylate according to the procedure described in Example 12. The title product was in the form of white crystals.

Yield: 77%

Specific rotation: $[\alpha]^{20}_D=+90.2°$ (c=0.5, methanol)

EXAMPLE 19

(R)-(−)-3,4Dihydro-2,4-dimethyl-3-oxo-2H-1,4-benzoxazine-2-carboxylic acid

A) This compound was prepared from (R)-(−)-methyl-3,4-dihydro-2,4-dimethyl-3-oxo-2H-1,4-benzoxazine-2-carboxylate according to the procedure described in Example 18. The title product was in the form of white crystals, m.p. 139°–142° C.

Yield: 86%

Specific rotation: $[\alpha]^{20}_D=-85.2°$ (c=0.5, methanol)

IR (KBr): ν=3412, 2483, 1973, 1681, 1610, 1501, 1450, 1391, 1275, 1243, 1155, 1032, 850, 761 cm$^{-1}$.

$^1$H-NMR (300 MHz, DMSO-d$_6$): δ=1.70 (s, 3H, CH$_3$), 3.31 (s, 3H, N—CH$_3$), 7.02–7.19 (m, 4H, 4H-arom.) ppm.

Analysis for C$_{11}$H$_{11}$NO$_4$ (221.21): calc.: 59.73% C 5.01% H 6.33% N found: 59.46% C 4.92% H 5.98% N B) Alternatively, this compound was prepared from (−)-1-phenylethylammonium 3,4-dihydro-2,4-dimethyl-3-oxo-2H-1,4-benzoxazine-2-carboxylate according to the procedure described in Example 12. The title product was in the form of white crystals.

Yield: 92%

Specific rotation: $[\alpha]^{20}_D = -83.3°$ (c=0.5, methanol)

EXAMPLE 20

Ethyl-3,4-dihydro-4-ethyl-2-methyl-3-oxo-2H-1,4-benzoxazine-2-carboxylate

The title compound was prepared from ethyl-3,4-dihydro-2-methyl-3-oxo-2H-1,4-benzoxazine-2-carboxylate and ethyl bromide according to the procedure described in Example 16. The title product was a viscous oil, which was purified by column chromatography (silica gel; dichloromethane/methanol 100:1).

Yield: 62%

IR (KBr): $\nu$=3624, 3360, 2980, 1752, 1691, 1610, 1501, 1466, 1397, 1274, 1241, 1124, 1047, 1017, 752 cm$^{-1}$.

Analysis for $C_{14}H_{17}NO_4$ (263.29): calc.: 63.87% C 6.51% H 5.32% N found: 63.82% C 6.64% H 5.72% N

EXAMPLE 21

3,4-Dihydro-4-ethyl-2-methyl-3-oxo-2H-1,4-benzoxazine-2-carboxylic acid

This compound was prepared from ethyl-3,4-dihydro-4-ethyl-2-methyl-3-oxo-2H-1,4-benzoxazine-2-carboxylate according to the procedure described in Example 18. The title product was in the form of white crystals, m.p. 164°–168° C.

Yield: 92%

IR (KBr): $\nu$=3503, 3436, 2997, 2581, 1743, 1637, 1496, 1420, 1249, 1138, 756, 589 cm$^{-1}$.

Analysis for $C_{12}H_{13}NO_4$ (235.24): calc.: 61.27% C 5.57% H 5.95% N found: 61.37% C 5.38% H 6.15% N

EXAMPLE 22

Methyl-4-benzyl-3,4-dihydro-2-methyl-3-oxo-2H-1,4-benzoxazine-2-carboxylate

This compound was prepared from methyl-3,4-dihydro-2-methyl-3-oxo-2H-1,4-benzoxazine-2-carboxylate and benzyl bromide according to the procedure described in Example 16. The product was in the form of white crystals, which were recrystallized from a mixture of hexane and diethyl ether, m.p. 113°–114° C.

Yield: 73%

IR (KBr): $\nu$=3479, 3356, 2943, 1752, 1695, 1607, 1499, 1432, 1392, 1332, 1251, 1124, 1017, 965, 916, 825, 738, 664 cm$^{-1}$.

$^1$H-NMR (300 MHz, DMSO-d$_6$): $\delta$=1.81 (s, 3H, CH$_3$), 3.66 (s, 3H, OCH$_3$), 5.00 (d, 1H$_A$, $^2J_{AB}$=16.3 Hz, CH$_2$-benzyl), 5.35 (d, 1H$_B$, $^2J_{AB}$=16.3 Hz, CH$_2$-benzyl), 6.94–7.12 (m, 4H, 4H-arom.), 7.23–7.37 (m, 5H, 5H-arom. (benzyl)) ppm.

Analysis for $C_{18}H_{17}NO_4$ (311.34): calc.: 69.44% C 5.50% H 4.50% N found: 69.07% C 5.35% H 5.21% N

EXAMPLE 23

4-Benzyl-3,4-dihydro-2-methyl-3-oxo-2H-1,4-benzoxazine-2-carboxylic acid

This compound was prepared from methyl-3,4-dihydro-2-methyl-3-oxo-2H-1,4-benzoxazine-2-carboxylate according to the procedure described in Example 18. After the acidification of the aqueous phase with 1M HCl, the title acid was extracted into ethyl acetate. The organic phase was dried over MgSO$_4$ and the solvent was evaporated. The title product was in the form of white crystals, m.p. 140°–144° C.

Yield: 95%

IR (KBr): $\nu$=3548, 3429, 2945, 2607, 1724, 1681, 1501, 1404, 1283, 1250, 1134, 956, 760, 694 cm$^{-1}$.

$^1$H-NMR (300 MHz, DMSO-d$_6$): $\delta$=1.79 (s, 3H, CH$_3$), 4.98 (d, 1H$_A$, $^2J_{AB}$=16.36 Hz, CH$_2$-benzyl), 5.36 (d, 1H$_B$, $^2J_{AB}$=16.36 Hz, CH$_2$-benzyl), 6.80–7.10 (m, 4H, 4H-arom.), 7.24–7.35 (m, 5H, 5H-arom. (benzyl)) ppm.

Analysis for $C_{17}H_{15}NO_4$ (297.31): calc.: 68.68% C 5.09% H 4.71% N found: 67.65% C 4.85% H 5.36% N

EXAMPLE 24

Ethyl-2-methyl-3,4-dihydro-3-oxo-2H-1,4-benzothiazine-2-carboxylate

To a suspension of KF (3.016 g, 52 mmoles) in anhydrous dimethyl formamide (14 ml), diethyl-2-bromo-2-methyl-malonate (3.90 ml, 20 mmoles) was added and the mixture was stirred for 15 minutes at room temperature. Subsequently, 2-mercaptoaniline (2.50 g, 20 mmoles) was added and the mixture was stirred for 6 hours at the temperature of 60° C. and overnight at room temperature. The reaction mixture was admixed with a mixture of water and ice (80 ml), the product which separated was filtered off by suction and recrystallized from absolute ethanol. Thus there were obtained 3.80 g (75.7%) of the title product in the form of white crystals, m.p. 109°–111° C.

IR (KBr): $\nu$=3448, 1743, 1665, 1588, 1484, 1381, 1238, 1119, 1010, 932, 858, 826, 747, 709, 681 cm$^{-1}$.

$^1$H-NMR (300 MHz CDCl$_3$): $\delta$=0.96–1.04 (t, 3H, CH$_3$, J=7.1 Hz), 1.78–1.82 (s, 3H, CH$_3$), 3.95–4.40 (m, 2H, CH$_2$), 6.85–7.35 (ABX$_3$ m, 4H, benzene), 8.75–8.95 (s, 1H, NH) ppm.

Analysis for $C_{12}H_{13}NO_3S$ (251): calc.: 57.37% C 5.18% H 5.58% N found: 57.52% C 4.89% H 5.58% N

EXAMPLE 25

2-Methyl-3,4-dihydro-3-oxo-2H-1,4-benzothiazine-2-carboxylic acid

Ethyl-2-methyl-3,4-dihydro-3-oxo-2H-1,4-benzothiazine-2-carboxylate (0.251 g, 1 mmole) and 1N NaOH (2.2 ml, 2.2 mmoles) were stirred in dioxan (5 ml) for 48 hours at room temperature. The solvent was evaporated, water (5 ml) was added to the residue and it was acidified with 20% HCl to pH=2. The crystals which separated were filtered off by suction and recrystallized from absolute ethanol. Thus there were obtained 0.234 g (98.0%) of the title product in the form of white crystals, m.p. 164–°165° C.

IR (KBr): $\nu$=2982, 1707, 1674, 1586, 1482, 1450, 1413, 1374, 1281, 1156, 1127, 1032, 890, 751, 658, 624 cm$^{-1}$.

$^1$H-NMR (300 MHz, DMSO-d$_6$): $\delta$=1.55–1.65 (s, 3H, CH$_3$), 6.95–7.35 (ABX$_3$, m, 4H, benzene), 10.75–10.85 (s, 1H, NH) ppm.

Analysis for $C_{10}H_9NO_3S$ (223): calc.: 53.81% C 4.04% H 6.28% N found: 54.41% C 3.47% H 5.70% N

EXAMPLE 26

Benzyl-N-(2-methyl-3-oxo-3,4-dihydro-2H-1,4-benzoxazine-2-carbonyl-L-alanyl-D-isoglutaminate To a solution of benzyl L-alanyl-D-isoglutaminate hydrochloride (970 mg, 2.82 mmoles) and 2-methyl-3,4-dihydro- 3-oxo-2H-1,4-benzoxazine-2-carboxylic acid (585 mg, 2.82 mmoles) in dry dimethylformamide (12 ml), diphenylphosphoryl azide (777 mg, 2.82 mmoles) was added with stirring on an ice bath, followed by the addition of triethylamine (571 mg, 5.65 mmoles). The stirring was continued for one hour on the ice bath and then for 48 hours at room temperature. Ethyl acetate (60 ml) was added thereto and the mixture was extracted with 10% citric acid (3×10 ml). The combined citric acid phases were re-extracted with ethyl acetate (6×25 ml). All six ethyl acetate phases were combined and successively washed with distilled water (3×10 ml), saturated NaCl solution (3×10 ml), saturated $NaHCO_3$ solution (3×10 ml), distilled water (3×10 ml) and saturated NaCl solution (3×10 ml). The mixture was dried over $MgSO_4$, the drying agent was filtered off and the solvent was evaporated, thus yielding 1.19 g (85%) of the title product in the form of a white foam, which was, by reprecipitation from a mixture of ethyl acetate and n-hexane, converted to the crystalline form, m.p. 146°–152° C.

IR (KBr): ν=3295, 1713, 1649, 1534, 1502, 1446, 1380, 1311, 1232, 1168, 1134, 1028, 955, 827, 755, 695, 663, 586, 524 $cm^{-1}$.

$^1$H-NMR (300 MHz, DMSO-$d_6$): δ=1.02 (1.20), (d, 3H, J=7.1 Hz, $CH_3$-Ala), 1.57 (1.63) (s, 3H, $CH_3$), 1.54–1.82 (m, 1H, $CH_2$-βiGln), 1.89–2.06 (m, 1H, $CH_2$-βiGln), 2.24–2.36 (m, 2H, $CH_2$-γiGln), 4.05–4.28 (m, 2H, CH-Ala, CH-iGln), 5.06 (5.07), (s, 2H, $CH_2$-benzyl), 6.80–7.20 (m, 5H, 4H-arom., NH), 7.20–7.45 (m, 6H, 5H-arom. (benzyl), NH), 7.64 (7.98) (d, 1H, J=8.1 Hz, NH), 8.10 (8.20) (d, 1H, J=7.4 Hz, NH), 10.75 (10.90) (s, 1H, NH) ppm.

Analysis for $C_{25}H_{28}N_4O_7$ (496.519): calc.: 60.48% C 5.68% H 11.28% N found: 60.21% C 5.58% H 11.04% N

EXAMPLE 27

N-(2-Methyl-3-oxo-3,4-dihydro-2H-1,4-benzoxazine-2-carbonyl)-L-alanyl-D-isoglutamine Benzyl-N-(2-methyl-3-oxo-3,4-dihydro-2H-1,4-benzoxazine-2-carbonyl)-L-alanyl-D-isoglutaminate (1640 mg, 3.30 mmoles) was dissolved in methanol (20 ml), Pd/C (10%, 170 mg) was added thereto and the mixture was hydrogenated at normal pressure for 1 hour. After the removal of the catalyst and evaporation of the solvent, 1275 mg (95%) of the title product in the form of a white foam were obtained.

IR (KBr): ν=3307, 2981, 1701, 1613, 1501, 1379, 1228, 1172, 1131, 954, 756, 577, 528 $cm^{-1}$.

$^1$H-NMR (300 MHz, DMSO-$d_6$): δ=1.05 (1.21) (d, 3H, J=7.0 Hz, $CH_3$-Ala), 1.60 (1.65) (s, 3H, $CH_3$), 1.58–1.76 (m, 1H, $CH_2$-βiGln), 1.58–2.01 (m, 1H, $CH_2$-βiGln), 2.11–2.22 (m, 2H, $CH_2$-γiGln), 4.10–4.30 (m, 2H, CH-Ala, CH-iGln), 6.84–7.18 (m, 5H, 4H-arom., NH), 7.28 (7.34) (s, 1H, NH), 7.65 (7.99) (d, 1H, J=8.2 Hz, NH), 8.13 (8.21) (d, 1H, J=7.4 Hz, NH), 10.77 (10.94) (s, 1H, NH), 12.10 (s, br, 1H, COOH) ppm.

Analysis for $C_{18}H_{22}N_4O_7$ (406.394): calc.: 53.19% C 5.46% H 13.78% N found: 53.47% C 5.76% H 13.60% N

EXAMPLE 28 trans-Dibenzyl-N-(2-methyl-3-oxo-octahydro-2H-1,4-benzoxazine-2-carbonyl)-L-alanyl-D-glutamate To a solution of dibenzyl-L-alanyl-D-glutamate hydrochloride (652 mg, 1.5 mmoles) and trans-2-methyl-3-oxo-octahydro-2H-1,4-benzoxazine-2-carboxylic acid (318 mg, 1.5 mmoles) in dry dimethylformamide (7 ml), diphenylphosphoryl azide (412 mg, 1.5 mmoles) was added with stirring on an ice bath, followed by the addition of triethylamine (303 mg, 3.0 mmoles). The stirring was continued for one hour on the ice bath and for 48 hours at room temperature. Ethyl acetate (40 ml) was added thereto and the mixture was successively washed with 10% citric acid (3×10 ml), distilled water (3×10 ml), saturated NaCl solution (3×10 ml), saturated $NaHCO_3$ solution (3×10 ml), distilled water (3×10 ml) and saturated NaCl solution (3×10 ml). The mixture was dried over $MgSO_4$, the drying agent was filtered off and the solvent was evaporated. The crude title product (770 mg, 82%) in the form of a white foam was purified by column chromatography (silica gel; chloroform/methanol= 9:1), yielding 720 mg of the pure product.

IR (NaCl-film): ν=3289, 2937, 2864, 1737, 1676, 1508, 1454, 1376, 1168, 739, 698, 533 $cm^{-1}$.

$^1$H-NMR (300 MHz, DMSO-$d_6$): δ=1.00–1.38 (m, 4H, $H_{ax}$), 1.22 (1.23) (d, 3H, J=6.8 Hz, $CH_3$-Ala), 1.46 (1.47) (s, 3H, $CH_3$), 1.50–1.75 (m, 4H, $H_{eq}$), 1.75–1.98 (m, 1H, $CH_2$-βGlu), 1.98–2.16 (m, 1H, $CH_2$-βGlu), 2.36–2.48 (m, 2H, $CH_2$-γGlu), 3.00–3.25 (m, 1H, CH), 3.30–3.50 (m, 1H, CH), 4.26–4.44 (m, 2H, CH-Ala, CH-Glu), 5.08 (s, 2H, $CH_2$-benzyl), 5.13 (s, 2H, $CH_2$-benzyl), 7.28–7.44 (m, 10H, H-arom.), 7.65–8.50 (7 m, 3H, NH) ppm.

Analysis for $C_{32}H_{39}N_3O_8$ (593.65): calc.: 64.74% C 6.62% H 7.08% N found: 64.69% C 6.84% H 6.99% N

EXAMPLE 29 trans-N-(2-Methyl-3-oxo-octahydro-2H-1,4-benzoxazine-2-carbonyl)-L-alanyl-D-glutamic acid trans-Dibenzyl-N-(2-methyl-3-oxo-octahydro-2H-1,4-benzoxazine-2-carbonyl)-L-alanyl-D-glutamate (700 mg, 1.179 mmoles) was dissolved in methanol (20 ml), Pd/C (10%, 110 mg) was added thereto and the mixture was hydrogenated at normal pressure for 1 hour. After the removal of the catalyst and evaporation of the solvent, 453 mg (93%) of the title product in the form of a white solid foam were obtained.

IR (KBr): ν=3318, 2843, 1737, 1668, 1521, 1450, 1375, 1216, 1169, 1110, 1069, 957, 634 $cm^{-1}$.

$^1$H-NMR (300 MHz, DMSO-$d_6$): δ=1.00–1.40 (m, 4H, $4H_{ax}$), 1.20 (1.45) (d, 3H, J=6.5 Hz, $CH_3$-Ala), 1.44 (1.46) (s, 3H, $CH_3$), 1.50–2.10 (m, 6H, $4H_{eq}$, $CH_2$-βGlu), 2.10–2.22 (m, 2H, $CH_2$-γGlu), 3.00–3.24 (m, 1H, CH), 3.24–3.55 (m, 1H, CH), 4.26–4.40 (m, 2H, CH-Ala, CH-Glu), 7.62–8.50 (6m, 3H, NH), 12.50 (s, 2H, COOH) ppm.

Analysis for $C_{18}H_{27}N_3O_8$ (413.427): calc.: 52.29% C 6.58% H 10.16% N found: 51.83% C 6.87% H 9.99% N

EXAMPLE 30

Dibenzyl-N-(2-methyl-3-oxo-3,4-dihydro-2H-1,4-benzoxazine-2-carbonyl)-L-alanyl-D-glutamate The compound was prepared from 2-methyl-3,4-dihydro-3-oxo-2H-1,4-benzoxazine-2-carboxylic acid according to the procedure described in Example 28. The title product was in the form of a viscous oil.

Yield: 89%

IR (NaCl-film): ν=3307, 3066, 2981, 1736, 1705, 1613, 1501, 1455, 1379, 1169, 956, 753, 698 $cm^{-1}$.

$^1$H-NMR (300 MHz, DMSO-$d_6$): δ=1.04 (1.22) (d, 3H, J=7.1 Hz, $CH_3$-Ala), 1.57 (1.65) (s, 3H, $CH_3$), 1.75–1.95 (m, 1H, $CH_2$-βGlu), 1.98–2.14 (m, 1H, $CH_2$-βGlu), 2.34–2.48

(m, 2H, CH$_2$-γGlu), 4.14–4.27 (m, 1H, CH-Glu), 4.27–4.40 (m, 1H, CH-Ala), 5.08 (s, 2H, CH$_2$-benzyl), 5.12 (5.13) (s, 2H, CH$_2$-benzyl), 6.81–7.13 (m, 4H, 4H-arom.), 7.25–7.45 (m, 10H, 10H-arom. (benzyl)), 7.91–8.04 (m, 1H, NH), 8.27–8.33. (m, 1H, NH), 10.78 (10.98) (s, 1H, NH) ppm.

Analysis for C$_{32}$H$_{33}$N$_3$O$_8$ (587.63)×H$_2$O: calc.: 63.46% C 5.83% H 6.94% N found: 63.11% C 5.94% H 6.84% N

EXAMPLE 31

Benzyl-N-(2-methyl-6-nitro-3-oxo-3,4-dihydro-2H-1,4-benzoxazine-2-carbonyl)-L-alanyl-D-isoglutaminate The compound was prepared from 2-methyl-6-nitro-3-oxo-3,4-dihydro-2H-1,4-benzoxazine-2-carboxylic acid according to the procedure described in Example 26. The title product was in the form of a solid yellow foam.

Yield: 72%

IR (KBr): ν=3342, 3072, 2954, 1718, 1666, 1530, 1454, 1345, 1284, 1243, 1170, 1121, 1088, 967, 889, 747, 699 cm$^{-1}$.

$^1$H-NMR (300 MHz, DMSO-d$_6$): δ=1.11 (1.21) (d, 3H, J=7.4 Hz, CH$_3$-Ala), 1.70 (1.72) (s, 3H, CH$_3$), 1.62–1.83 (m, 1H, CH$_2$-βiGln), 1.90–2.08 (m, 1H, CH$_2$-βiGln), 2.25–2.38 (m, 2H, CH$_2$-γiGln), 4.12–4.28 (m, 2H, CH-Ala, CH-iGln), 5.07 (s, 2H, CH$_2$-benzyl), 7.13–7.44 (m, 8H, 5H-arom., H-arom., 2-NH), 7.73 (7.74) (d, 1H, J=2.64 Hz, H-arom.), 7.82–8.08 (m, 2H, H-arom., NH), 8.32 (8.35) (d, 1H, J=6.8 Hz, NH), 11.22 (11.34) (s, 1H, NH) ppm.

Analysis for C$_{25}$H$_{27}$N$_5$O$_9$ (541.516): calc.: 55.45% C 5.03% H 12.93% N found: 54.72% C 5.23% H 12.50% N

EXAMPLE 32

N-(2-Methyl-6-nitro-3-oxo-3,4-dihydro-2H-1,4-benzoxazine-2-carbonyl)-L-alanyl-D-isoglutamine The compound was prepared from benzyl-N-(2-methyl-6-nitro-3-oxo-3,4-dihydro-2H-1,4-benzoxazine-2-carbonyl)-L-alanyl-D-isoglutaminate according to the procedure described in Example 27. The title product was in the form of a solid brown foam.

Yield: 90% m.p.: 142°–146° C.

IR (KBr): ν=3718–3080, 2931, 1698, 1519, 1448, 1379, 1228, 1172, 1134, 948, 858, 815 cm$^{-1}$.

$^1$H-NMR (300 MHz DMSO-d$_6$): δ=1.05 (2.43) (d, 3H, J=7.0 Hz, CH$_3$-Ala), 1.52 (1.58) (s, 1H, CH$_2$-βiGln), 1.86–2.02 (m, 1H, CH$_2$-βiGln), 2.08–2.28 (m, 2H, CH$_2$-γiGln), 4.05–4.30 (m, 2H, CH-Ala, CH-iGln), 6.13 (d, 2H, J=7.7 Hz, H-arom.), 6.70–6.78 (m, 1H, H-arom.), 7.08 (7.12) (s, 1H, NH), 7.25 (7.33) (s, 1H, NH), 7.65 (7.95) (d, 1H, J=8.4 Hz, NH), 7.99 (8.09) (d, 1H, J=7.5 Hz, NH), 10.49 (10.68) (s, 1H, NH) ppm.

Analysis for C$_{18}$H$_{21}$N$_5$O$_9$ (451.392): calc.: 47.90% C 4.69% H 15.51% N found: 48.18% C 4.84% H 15.16% N

EXAMPLE 33

Dibenzyl-N-(2-methyl-7-nitro-3-3,4-dihydro-2H-1,4-benoxazine-2-carbonyl)-L-alanyl-D-glutamate The compound was prepared from 2-methyl-7-nitro-3-oxo-3,4-dihydro-2H-1,4-benzoxazine-2-carboxylic acid according to the procedure described in Example 28. The title product was in the form of a viscous oil.

Yield: 69%

IR (NaCl-film): ν=3315, 2939, 1731, 1660, 1607, 1531, 1454, 1378, 1327, 1239, 1168, 744,698 cm$^{-1}$.

$^1$H-NMR (300 MHz DMSO-d$_6$): δ=1.07 (1.21) (d, 3H, J=7.2 Hz, CH$_3$-Ala), 1.68 (1.70) (s, 3H, CH$_3$), 1.64–2.13 (m, 2H, CH$_2$-βGlu), 2.30–2.47 (m, 2H, CH$_2$-γGlu), 4.15–4.43 (m, 2H, CH-Ala, CH-Glu), 5.06 (s, 2H, CH$_2$-benzyl), 5.08 (s, 2H, CH$_2$-benzyl), 7.04 (7.07) (d, 1H, J=8.5 Hz, H-arom.), 7.26–7.48 (m, 10H, 10H-arom. (benzyl)), 7.86–8.41 (2m, 4H, 2H-arom., 2NH), 11.44 (s, br, 1H, NH) ppm.

Analysis for C$_{32}$H$_{32}$N$_4$O$_{10}$ (632.626): calc.: 60.76% C 5.10% H 8.86% N found: 61.05% C 5.56% H 8.68% N

EXAMPLE 34

N-(2-Methyl-7-nitro-3-oxo-3,4-dihydro-2H-1,4-benzoxazine-2-carbonyl)-L-alanyl-D-glutamic acid The compound was prepared from dibenzyl-N-(2-methyl-7-nitro-3-oxo-3,4-dihydro-2H-1,4-benzoxazine-2-carbonyl)-L-alanyl-D-glutamate according to the procedure described in Example 29. The title product was in the form of a solid brown foam.

Yield: 86% m.p.: 132°–135° C.

IR (KBr): ν=3707–2672, 1706, 1519, 1381, 1248, 1175, 1131, 982, 815 cm$^{-1}$. $^1$H-NMR (300 MHz, DMSO-d$_6$): δ=1.08 (1.23) (d, 3H, J=7 Hz, CH$_3$-Ala), 1.51 (1.59) (s, 3H, CH$_3$), 1.68–1.88 (m, 1H, CH$_2$-βGlu), 1.88–2.08 (m, 1H, CH$_2$-βGlu), 2.08–2.36 (m, 2H, CH$_2$-γGlu), 4.10–3.39 (m, 2H, CH-Ala, CH-Glu), 6.14–6.60 (m, 2H, 2H-arom.), 7.00–8.20 (m, 3H, H-arom., 2NH), 10.30 (10.60) (s, 1H, NH), 16.00 (s, br, 2H, COOH) ppm.

Analysis for C$_{18}$H$_{20}$N$_4$O$_{10}$ (452.377): calc.: 47.79% C 4.46% H 12.38% N found: 47.80% C 4.89% H 11.95% N

EXAMPLE 35

Dibenzyl-N-(2,6-dimethyl-3-oxo-3,4-dihydro-2H-1,4-benzoxazine-2-carbonyl)-L-alanyl-D-glutamate The compound was prepared from 2,6-dimethyl-3,4-dihydro-3-oxo-2H-1,4-benzoxazine-2-carboxylic acid according to the procedure described in Example 28. The title product was in the form of a viscous oil.

Yield: 61%

IR (NaCl-film): ν=3310, 2938, 1738, 1704, 1519, 1454, 1378, 1233, 1168, 751, 698 cm$^{-1}$.

$^1$H-NMR (300 MHz, DMSO-d$_6$): δ=1.04 (1.21) (d, 3H, J=7.1 Hz, CH$_3$-Ala), 1.55 (1.62) (s, 3H, CH$_3$), 1.67–1.94 (m, 1H, CH$_2$-βGlu), 1.94–2.13 (m, 1H, CH$_2$-βGlu), 2.16 (2.20) (s, 3H, CH$_3$), 2.32–2.48 (m, 2H, CH$_2$-γGlu), 4.12–4.26 (m, 1H, CH-Glu), 4.26–4.38 (m, 1H, CH-Ala), 5.07 (s, 2H, CH$_2$-benzyl), 5.11 (s, 2H, CH$_2$-benzyl), 6.66 (s, 1H, H-arom.), 6.62–6.78 (m, 1H, H-arom.), 6.90 (6.96) (d, 1H, J=8.0 Hz, H-arom.), 7.28–7.46 (m, 10H, 10H-arom.), 7.86 (7.98) (d, 1H, J=7.8 Hz, NH), 8.24 (8.32) (d, 1H, J=7.4 Hz, NH), 10.72 (10.88) (s, 1H, NH) ppm.

Analysis for C$_{33}$H$_{35}$N$_3$O$_8$ (601.63): calc.: 65.88% C 5.86% H 6.98% N found: 65.47% C 5.98% H 6.63% N

EXAMPLE 36

N-(2,6-Dimethyl-3-oxo-3,4-dihydro-2H-1,4-benzoxazine-2-carbonyl)-L-alanyl-D-glutamic acid The compound was prepared from dibenzyl-N-(2,6-dimethyl-3-oxo-3,4-dihydro-2H-1,4-benzoxazine-2-carbonyl)-L-alanyl-D-glutamate according to the procedure described in Example 29. The title product was in the form of a solid foam.

Yield: 87%

IR (KBr): ν=3742–2602, 1698, 1520, 1450, 1382, 1232, 1173, 1134, 816 cm$^{-1}$.

$^1$H-NMR (300 MHz, DMSO-d$_6$): δ=1.05 (1.23) (d, 3H, J=7.1 Hz, CH$_3$-Ala), 1.58 (1.63) (s, 3H, CH$_3$), 1.55–1.82 (m, 1H, CH$_2$-βGlu), 1.88–2.06 (m, 1H, CH$_2$-βGlu), 2.20 (s, 3H, CH$_3$-arom.), 2.14–2.32 (m, 2H, CH$_2$-γGlu), 4.10–4.27 (m, 2H, CH-Ala, CH-Glu), 6.67 (s, 1H, H-arom.), 6.70–6.78 (m, 1H, H-arom.), 6.92 (6.96) (d, 1H, J=8.1 Hz, H-arom.), 7.70 (8.10) (d, 1H, J=8.1 Hz, NH), 7.96 (8.16) (d, 1H, J=7.6 Hz, NH), 10.70 (10.85) (s, 1H, NH), 12.40 (s, br, 2H, 2COOH) ppm.

Analysis for C$_{19}$H$_{23}$N$_3$O$_8$ (421.406)×H$_2$O: calc.: 51.93% C 5.73% H 9.56% N found: 52.04% C 5.96% H 9.86% N

EXAMPLE 37

Dibenzyl-N-(2-methyl-3-oxo-3,4-dihydro-2H-pyrido[3,2-b]-1,4-oxazine-2-carbonyl)-L-alanyl-D-glutamate The compound was prepared from 2-methyl-3,4dihydro-3-oxo-2H-pyrido[3,2-b]-1,4-oxazine-2-carboxylic acid according to the procedure described in Example 28.

Yield: 45% m.p.: 93°–95° C.

IR (KBr): ν=3322, 1732, 1646, 1532, 1463, 1378, 1349, 1272, 1163, 955, 799, 752, 697, 590 cm$^{-1}$.

$^1$H-NMR (300 MHz, DMSO-d$_6$): δ=1.07 (2.40) (d, 3H, J=7.1 Hz, CH$_3$-Ala), 1.61 (1.66) (s, 3H, CH$_3$), 1.78–1.96 (m, 1H, CH$_2$-βGlu), 1.96–2.14 (m, 1H, CH$_2$-βGlu), 2.34–2.48 (m, 2H, CH$_2$-γGlu), 4.17–4.27 (m, 1H, CH-Glu), 4.27–4.40 (m, 1H, CH-Ala), 5.08 (s, 2H, CH$_2$-benzyl), 5.11 (s, 2H, CH$_2$-benzyl), 6.92–7.06,(m, 1H, H$_7$), 7.28–7.53 (m, 11H, 10H-arom., H$_8$), 7.91 (7.96) (dd, 1H, J$_{6,7}$=4.8 Hz, J$_{6,8}$=1.4 Hz, H$_6$), 8.02 (8.04) (d, 1H, J=7.5 Hz, NH), 8.34 (8.38) (d, 1H, J=7.8 Hz, NH), 11.38 (11.50) (s, 1H, NH) ppm.

Analysis for C$_{31}$H$_{32}$N$_4$O$_8$ (588.616): calc.: 63.26% C 5.48% H 9.52% N found: 63.50% C 5.62% H 9.45% N

EXAMPLE 38

N-(2-methyl-3-oxo-3,4dihydro-2H-pyrido[3,2-b]-1,4-oxazine-2-carbonyl)-L-alanyl-D-glutamic acid The compound was prepared from dibenzyl-N-(2-methyl-3-oxo-3,4-dihydro-2H-pyrido[3,2-b]-1,4-oxazine-2-carbonyl)-L-alanyl-D-glutamate according to the procedure described in Example 29. The title product was in the form of a solid foam.

Yield: 94%

IR (KBr): ν=3683–2672 (br), 2355, 1716, 1661, 1540, 1463, 1379, 1351, 1215, 959, 802, 752 cm$^{-1}$.

$^1$H-NMR (300 MHz, DMSO-d$_6$): δ=1.09 (1.60) (d, 3H, J=7.1 Hz, CH$_3$-Ala), 1.65 (1.67) (s, 3H, CH$_3$), 1.60–1.86 (m, 1H, CH$_2$-βGlu), 1.89–2.06 (m, 1H, CH$_2$-βGlu), 2.18–2.30 (m, 2H, CH$_2$-γGlu), 4.14–4.29 (m, 2H, CH-Ala, CH-Glu), 6.97–7.05 (m, 1H, H$_7$), 7.42 (7.49) (dd, 1H, J$_{7,8}$=8.0 Hz, J$_{6,8}$=1.4 Hz, H$_8$), 7.93 (7.95) (dd, 1H, J$_{6,7}$=4.9 Hz, J$_{6,8}$=1.4 Hz, H$_6$), 7.85 (8.11) (d, 1H, J=7.6 Hz, NH), 8.14 (8.22) (d, 1H, J=7.5 Hz, NH), 11.34 (11.48) (s, 1H, NH), 12.40 (s, br, 2H, 2COOH) ppm.

EXAMPLE 39

Dibenzyl-N-(2,4-dimethyl-3-oxo-3,4-dihydro-2H-1,4-benzoxazine-2-carbonyl)-L-alanyl-D-glutamate The compound was prepared from 2,4-dimethyl-3,4-dihydro-3-oxo-2H-1,4-benzoxazine-2-carboxylic acid according to the procedure described in Example 28.The title product was in the form of a viscous oil.

Yield: 82%

IR (NaCl-film): ν=3328, 3000, 1738, 1684, 1504, 1455, 1384, 1241, 1167, 1042, 956, 752, 699 cm$^{-1}$.

$^1$H-NMR (300 MHz, DMSO-d$_6$): δ=1.00 (1.20) (d, 3H, J=7.1 Hz, CH$_3$-Ala), 1.59 (1.67) (s, 3H, CH$_3$), 1.72–1.94 (m, 1H, CH$_2$-βGlu), 1.95–2.13 (m, 2H, CH$_2$-βGlu), 2.32–2.45 (m, 2H, CH$_2$-γGlu), 3.26 (3.28) (s, 3H, N—CH$_3$), 4.08–4.42 (m, 1H, CH-Glu), 4.26–4.40 (m, 1H, CH-Ala), 5.09 (s, 2H, CH$_2$-benzyl), 5.11 (s, 2H, CH$_2$-benzyl), 6.94–7.20 (m, 4H, H-arom.), 7.22–7.50 (m, 10H, H-arom. (benzyl)), 7.82 (8.06) (d, 1H, J=7.0 Hz, NH), 8.24 (8.29) (d, 1H, J=7.0 Hz, NH) ppm.

Analysis for C$_{33}$H$_{35}$N$_3$O$_8$ (601.655): calc.: 65.88% C 5.86% H 6.98% N found: 65.42% C 5.95% H 7.14% N

EXAMPLE 40

N-(2,4-Dimethyl-3-oxo-3,4-dihydro-2H-1,4-benzoxazine-2-carbonyl)-L-alanyl-D-glutamic acid The compound was prepared from dibenzyl-N-(2,4-dimethyl-3-oxo-3,4-dihydro-2H-1,4-benzoxazine-2-carbonyl)-L-alanyl-D-glutamate according to the procedure described in Example 29. The title product was in the form of a viscous oil.

Yield: 71%

IR (NaCl-film): ν=3718–2614 (br), 1686, 1503, 1388, 1240, 1042, 755 cm$^{-1}$.

$^1$H-NMR (300 MHz, DMSO-d$_6$): δ=1.01 (1.22) (d, 3H, J=7.1 Hz, CH$_3$-Ala), 1.62 (1.68) (s, 3H, CH$_3$), 1.56–1.82 (m, 1H, CH$_2$-βGlu), 1.87–2.06 (m, 1H, CH$_2$-βGlu), 2.15–2.33 (m, 2H, CH$_2$-γGlu), 3.17 (s, 3H, N—CH$_3$), 4.07–4.26 (m, 2H, CH-Ala, CH-Glu), 6.99–7.20 (m, 4H, 4H-arom.), 7.69 (8.20) (d, 1H, J=8.1 Hz, NH), 8.06 (8.10) (d, 1H, J=8.0 Hz, NH), 12.42 (s, br, 2H, 2COOH) ppm.

Analysis for C$_{19}$H$_{23}$N$_3$O$_8$ (421.406)×H$_2$O: calc.: 51.92% C 5.73% H 9.56% N found: 52.34% C 5.68% H 9.75% N

EXAMPLE 41

Benzyl-N-(6-chloro-2-methyl-3-oxo-3,4-dihydro-2H-1,4-benzoxazine-2-carbonyl)-L-alanyl-D-isoglutaminate The compound was prepared from 6-chloro-2-methyl-3,4-dihydro-3-oxo-2H-1,4-benzoxazine-2-carboxylic acid according to the procedure described in Example 26.

Yield: 69% m.p.: 106°–110° C.

IR (KBr): ν=3316, 3064, 2941, 1707, 1666, 1610, 1496, 1453, 1378, 1228, 1170, 1131, 1083, 934, 834, 813, 739, 698 cm$^{-1}$.

$^1$H-NMR (300 MHz, DMSO-d$_6$): δ=1.07 (1.21) (d, 3H, J=7.0 Hz, CH$_3$-Ala), 1.61 (1.65) (s, 3H, CH$_3$), 1.50–1.85 (m, 1H, CH$_2$-βiGln), 1.90–2.08 (m, 2H, CH$_2$-βiGln), 2.22–2.42 (m, 2H, CH$_2$-γiGln), 4.08–4.30 (m, 2H, CH-Ala, CH-iGln), 5.08 (s, 2H, CH$_2$-benzyl), 6.88 (6.89) (s, 1H, NH), 6.95–7.26 (m, 3H, 3H-arom.), 7.26–7.50 (m, 6H, 5H-arom., NH), 7.68 (8.00) (d, 1H, J=8.2 Hz, NH), 8.24 (8.28) (d, 1H, J=6.7 Hz, NH), 10.94 (11.06) (s, 1H, NH) ppm.

Analysis for C$_{25}$H$_{27}$N$_4$O$_7$Cl (530.964) calc.: 56.55% C 5.13% H 10.55% N found: 56.22% C 5.33% H 10.74% N

EXAMPLE 42

Benzyl-N-(3,4-dihydro-2,4-dimethyl-3-oxo-2H-1,4-benzoxazine-2-carbonyl)-L-alanyl-D-isoglutaminate The compound was prepared from 3,4-dihydro-2,4-dimethyl-3-oxo-2H-1,4-benzoxazine-2-carboxylic acid according to the procedure described in Example 26. The title product was in the form of a white foam, which was purified by column chromatography (silica gel; chloroform/methanol=9:1). The compound had no sharp melting point.

Yield: 60%

$^1$H-NMR (300 MHz, DMSO-d$_6$): δ=1.05 (1.23) (d, 3H, J=7.0 Hz, CH$_3$-Ala), 1.66 (1.75) (s, 3H, CH$_3$), 1.70–1.83 (m, 1H, CH$_2$-βiGln), 1.95–2.10 (m. 1H, CH$_2$-βiGln), 2.32 (2.35) (t, 2H, CH$_2$-γiGln), 3.30 (3.33) (s, 3H, N—CH$_3$), 4.10–4.30 (m, 2H, CH-Ala, CH-iGln), 5.10 (5.11) (s, 2H, CH$_2$-benzyl), 7.0–7.20 (m, 5H, 4H-arom., NH), 7.20–7.40 (m, 6H, 5H-arom. (benzyl), NH), 7.55 (7.90) (d, 1H, J=8.25 Hz, NH), 8.10 (8.20) (d, 1H, J=7.38 Hz, NH) ppm.

Analysis for C$_{26}$H$_{30}$N$_4$O$_7$ (510.55): calc.: 61.17% C 5.92% H 10.97% N found: 61.05% C 5.89% H 10.66% N

EXAMPLE 43

N-(3,4-Dihydro-2,4-dimethyl-3-oxo-2H-1,4-benzoxazine-2-carbonyl)-L-alanyl-D-isoglutamine The compound was prepared from benzyl-N-(3,4-dihydro-2,4-dimethyl-3-oxo-2H-1,4-benzoxazine-2-carbonyl)-L-alanyl-D-isoglutaminate according to the procedure described in Example 27. The title product was in the form of a white foam, which was converted to the crystalline form by reprecipitation from anhydrous ether. The compound had no sharp melting point.

Yield: 90%

IR (KBr): ν=3620–3150, 1667, 1504, 1388, 1240, 1141, 759 cm$^{-1}$.

$^1$H-NMR (300 MHz, DMSO-d$_6$): δ=1.02 (1.22) (d, 3H, J=6.9 Hz, CH$_3$-Ala), 1.63 (1.68) (s, 3H, CH$_3$), 1.68–1.80 (m, 1H, CH$_2$-βiGln), 1.83–2.02 (m, 1H, CH$_2$-βiGln), 2.10–2.22 (m, 2H, CH$_2$-γiGln), 3.30 (3.31) (s, 3H, N—CH_), 4.06–4.26 (m, 2H, CH-Ala, CH-iGln), 7.00–7.18 (m, 5H, 4H-arom., NH), 7.24 (7.32) (s, 1H, NH), 7.58 (7.92) (d, 1H, J=8.25 Hz, NH), 8.19 (8.24) (d, 1H, J=7.38 Hz, NH), 12.04 (s, broad, 1H, COOH) ppm.

Analysis for C$_{19}$H$_{24}$N$_4$O$_7$ · 0.6H$_2$O (431.22): calc.: 52.92% C 5.89% H 12.99% N found: 53.29% C 5.90% H 12.39% N

EXAMPLE 44

Benzyl-N-(3,4-dihydro-2,6-dimethyl-3-oxo-2H-1,4-benzoxazine-2-carbonyl)-L-alanyl-D-isoglutaminate The compound was prepared from 3,4-dihydro-2,6-dimethyl-3-oxo-2H-1,4-benzoxazine-2-carboxylic acid according to the procedure described in Example 26. The title product was in the form of a white foam, which was purified by column chromatography (silica gel; chloroform/methanol=9:1) and converted to the crystalline form by reprecipitation from anhydrous ether. The compound had no sharp melting point.

Yield: 71%

$^1$H-NMR (300 MHz, DMSO-d$_6$): δ=1.06 (1.24) (d, 3H, J=7.0 Hz, CH$_3$-Ala), 1.62 (1.69) (s, 3H, 2-CH$_3$), 1.65–1.88 (m, 1H, CH$_2$-βiGln), 1.90–2.10 (m, 1H, CH$_2$-βiGln), 2.21 (2.22) (s, 3H, 6-CH$_3$), 2.28–2.42 (m, 2H, CH$_2$-γiGln), 4.10–4.30 (m, 2H, Ch-Ala, CH-iGln), 5.10 (s, 2H, CH$_2$-benzyl), 6.68 (s, 1H, 5-H), 6.70–6.78 (m, 1H, 7/8-H), 6.95 (dd, 1H, 7/8-H), 7.12 (7.16) (s, 1H, NH), 7.26–7.42 (m, 6H, 5H-benzyl, NH), 7,62 (7.98) (d, 1H, J=8.2 Hz, NH), 8.12 (8.18) (d, 1H, J=7.4 Hz, NH), 10.68 (10.85) (s, 1H, 4-H) ppm.

Analysis for C$_{26}$H$_{30}$N$_4$O$_7$ (510.55): calc.: 61.17% C 5.92% H 10.97% N found: 60.54% C 5.77% H 10.71% N

EXAMPLE 45

N-(3,4-Dihydro-2,6-dimethyl-3-oxo-2H-1,4-benzoxazine-2-carbonyl)-L-alanyl-D-isoglutamine The compound was prepared from benzyl-N-(3,4-dihydro-2,6-dimethyl-3-oxo-2H-1,4-benzoxazine-2-carbonyl)-L-alanyl-D-isoglutaminate according to the procedure described in Example 27. The title product was in the form of a white foam, which was converted to the crystalline form by reprecipitation from anhydrous ether. The compound had no sharp melting point.

Yield: 92%

IR (KBr): ν=3600–3100, 2950–2500, 1699, 1519, 1447, 1383, 1232, 1172, 1134, 945, 815 cm$^{-1}$.

$^1$H-NMR (300 MHz, DMSO-d$_6$): δ=1.06 (1.25) (d, 3H, J=6.9 Hz, CH$_3$-Ala), 1.60 (1.68) (s, 3H, 2-CH$_3$), 1.68–1.80 (m, 1H, CH$_2$-βiGln), 1.83–2.08 (m, 1H, CH$_2$-βiGln), 2.10–2.22 (m, 2H, CH$_2$-γiGln), 2.20 (s, 3H, 6-CH$_3$), 4.10–4.28 (m, 2H, CH-Ala, CH-iGln), 6.68 (s, 1H, 5-H), 6.70–6.78 (m, 1H, 7/8-H), 6.95 (dd, 1H, 7/8-H), 7.12 (7.14) (s, 1H, NH), 7.32 (7.34) (s, 1H, NH), 7.58 (7.98) (d, 1H, J=8.2 Hz, NH), 8.14 (8.22) (d, 1H, J=7.4 Hz, NH), 10.70 (10.88) (s, 1H, 4-H), 12.1 (s-broad, 1H, COOH) ppm.

Analysis for C$_{19}$H$_{24}$N$_4$O$_7$ (420.41): calc.: 54.28% C 5.75% H 13.33% N found: 54.02% C 6.01% H 12.78% N

EXAMPLE 46

Benzyl-N-(3,4-dihydro-2-methyl-3-oxo-2H-1,4-benzothiazine-2-carbonyl)-L-alanyl-D-isoglutaminate 3,4-Dihydro-2-methyl-3-oxo-2H-1,4-benzothiazine-2-carboxylic acid (335 mg, 1.5 mmoles) and benzyl-L-alanyl-D-isoglutaminate hydrochloride (515 mg, 1.5 mmoles) were dissolved in anhydrous dimethylformamide (8 ml) and cooled to −10° C. on an ice bath. Diphenylphosphoryl azide (495 mg, 1.9 mmoles) and triethylamine (334 mg, 33 mmoles) were successively added thereto with stirring. The reaction mixture was stirred for 2 hours at −5° C. and then for 48 hours at room temperature. The reaction mixture was diluted with ethyl acetate (150 ml) and successively washed with 10% citric acid (24 ml), water (12 ml), saturated NaCl solution (12 ml), saturated NaHCO$_3$ solution (24 ml), water (24 ml) and saturated NaCl solution (24 ml). The organic phase was dried over anhydrous MgSO$_4$, filtered and the solvent was evaporated. The obtained product was quenched with ether and filtered off by suction. Thus there were obtained 550 mg (71.6%) of the title product in the form of a white powder, m.p. 89°–91° C.

IR (KBr): ν=3418, 2973, 1735, 1682, 1517, 1482, 1153, 1341, 1235, 1165 cm$^{-1}$.

$^1$H-NMR (300 MHz, DMSO-d$_6$): δ=0.95 (1.18) (d, 3H, J=7.1 Hz, CH$_3$-Ala), 1.55 (1.65) (s, 3H, CH$_3$), 1.65–1.85 (1.85–2.10) (m, 2H, CH$_2$-βiGln), 2.20–2.40 (m, 2H, CH$_2$-γiGln), 4.00–4.25 (m, 2H, CH-Ala, CH-iGln), 5.06 (5.07) (s, 2H, CH$_2$-benzyl), 6.90–7.25 (m, 5H, 4H aromatic, NH), 7.25–7.50 (m, 6H, 5H benzyl, NH), 7.80 (8.05) (d, 1H, J=8.3 Hz, NH), 8.15 (8.32) (d, 1H, J=7.4 Hz, NH), 10.75 (10.90) (s, 1H), NH) ppm.

Analysis for C$_{25}$H$_{28}$N$_4$O$_6$S (512): calc.: 58.59% C 5.47% H 10.94% N found: 58.25% C 5.49% H 10.80% N

EXAMPLE 47

N-(3,4-Dihydro-2-methyl-3-oxo-2H-1,4-benzothiazine-2-carbonyl)-L-alanyl-D-iso-glutamine Benzyl-N-(3,4-dihydro-2-methyl-3-oxo-2H-1,4-benzothiazine-2-carbonyl)-L-alanyl-D-isoglutaminate (485 mg, 1.06 mmoles) was dissolved in methanol (17 ml), Pd/C (10%, 75 mg) was added thereto and it was hydrogenated at normal pressure for 12 hours. After the removal of the catalyst and evaporation of the solvent, there were obtained 265 mg (59.3%) of the title product in the form of a white powder, m.p. 124°–125° C.

IR (KBr): ν=3406, 2978, 1678, 1654, 1519, 1472, 1237, 756 cm$^{-1}$.

$^1$H-NMR (300 MHz, DMSO-d$_6$): δ=0.98 (1.08) (d, 3H, J=7.1 Hz, CH$_3$-Ala), 1.05 (1.15) (s, 3H, CH$_3$), 1.65–1.85 (1.85–2.05) (m, 2H, CH$_2$-βiGln), 1.70–2.05 (2.05–2.30). (m, 2H, CH$_2$-γiGln), 4.00–4.35 (m, 2H, CH-Ala and CH-iGln), 6.90–7.40 (m, 5H, 4H arom., NH), 7.78 (8.05) (d, 1H, J=8.3 Hz, NH), 8.13 (8.31) (d, 1H, J=7.5 Hz, NH), 10.75 (10.90) (s, 1H, NH), 12.05 (s, 1H, COOH) ppm.

Analysis for C$_{18}$H$_{22}$N$_4$O$_6$S. H$_2$O (440): calc.: 49.09% C 5.45% H 12.73% N found: 49.55% C 5.63% H 12.88% N

EXAMPLE 48

(2R)-(+)-Benzyl-N-(3,4-dihydro-2-methyl-3-oxo-2H-1,4-benzoxazine-2-carbonyl)-L-alanyl-D-isoglutaminate The compound was prepared from (S)-(+)-3,4-dihydro-2-methyl-3-oxo-2H-1,4-benzoxazine-2-carboxylic acid according to the procedure described in Example 26. The title product was in the form of a white foam, which was purified by column chromatography (silica gel; chloroform/methanol=20:1) and converted to the crystalline form by reprecipitation from anhydrous ether. The compound had no sharp melting point.

Yield: 63%

Specific rotation: [α]$^{20}_D$=+17.0° (c=1.402, THF)

$^1$H-NMR (300 MHz, DMSO-d$_6$): δ=1.06 (d, 3H, J=7.09 Hz, CH$_3$-Ala), 1.66 (s, 3H, CH$_3$), 1.70–1.83 (m, 1H, CH$_2$-βiGln), 1.95–2.10 (m, 1H, CH$_2$-βiGln), 2.30–2.38 (t, 2H, CH$_2$-γiGln), 4.10–4.28 (m, 2H, CH-Ala, CH-iGln), 5.08 (s, 2H, CH$_2$-benzyl), 6.85–7.13 (m, 5H, 4H-arom., NH), 7.32–7.43 (m, 6H, 5H-arom. (benzyl), NH), 7.99 (d, 1H, J=8.25 Hz, NH), 8.12 (d, 1H, J=7.38 Hz, NH), 10.78 (s, 1H, NH) ppm.

Analysis for C$_{25}$H$_{28}$N$_4$O$_7$ (496.5): calc.: 60.48% C 5.68% H 11.28% N found: 59.99% C 5.52% H 10.78% N

EXAMPLE 49

(2S)-(+)-Benzyl-N-(3,4-dihydro-2-methyl-3-oxo-2H-1,4-benzoxazine-2-carbonyl)-L-alanyl-D-isoglutaminate The compound was prepared from (R)-(−)-3,4-dihydro-2-methyl-3-oxo-2H-1,4-benzoxazine-2-carboxylic acid according to the procedure described in Example 26. The title product was in the form of a white foam, which was purified by column chromatography (silica gel; chloroform/methanol=9:1) and converted to the crystalline form by reprecipitation from anhydrous ether. The compound had no sharp melting point.

Yield: 70%

Specific rotation: [α]$^{20}_D$=+20.0° (c=1.54, THF)

$^1$H-NMR (300 MHz, DMSO-d$_6$): δ=1.26 (d, 3H, J=7.09 Hz, CH$_3$-Ala), 1.60 (s, 3H, CH$_3$), 1.70–1.83 (m, 1H, CH$_2$-βGln), 1.95–2.10 (m, 1H, CH$_2$-βiGln), 2.28 (t, 2H, CH$_2$-γiGln), 4.10–4.28 (m, 2H, CH-Ala, CH-iGln), 5.05 (s, 2H, CH$_2$-benzyl), 6.85–7.10 (m, 4H, 4H-arom.), 7.30 (s, 1H, NH), 7.32–7.45 (m, 6H, 5H-arom. (benzyl), NH), 7.60 (d, 1H, J=8.25 Hz, NH), 8.15 (d, 1H, J=7.38 Hz, NH), 10.92 (s, 1H, NH) ppm.

EXAMPLE 50

(2R)-(+)-N-(3,4-Dihydro-2-methyl-3-oxo-2H-1,4-benzoxazine-2-carbonyl)-L-alanyl-D-isoglutamine The compound was prepared from (2R)-(+)-benzyl-N-(3, 4dihydro-2-diethyl-3-oxo-2H-1,4-benzoxazine-2-carbonyl)-L-alanyl-D-isoglutaminate according to the procedure described in Example 27. The title product was in the form of a white foam, which was converted to the crystalline form by reprecipitation from anhydrous ether. The compound had no sharp melting point.

Yield: 92%

Specific rotation: [α]$^{20}_D$=+21.15° (c=1.15, THF)

IR (KBr): ν=3600–3150, 3000–2500, 1702, 1501, 1381, 1229, 1175, 1134, 958, 759 cm$^{-1}$.

$^1$H-NMR (300 MHz, DMSO-d$_6$): δ=1.06 (d, 3H, J=6.9 Hz, CH$_3$-Ala), 1.67 (s, 3H, CH$_3$), 1.65–1.80 (m, 1H, CH$_2$-βiGln), 1.85–2.05 (m, 1H, CH$_2$-βiGln), 2.18 (t, 2H, CH$_2$-γiGln), 4.10–4.22 (m, 2H, CH-Ala, CH-iGln), 6.85–7.02 (m, 3H, 3H-arom.), 7.05 (m, 1H, 1H-arom.), 7.15 (s, 1H, NH), 7.32 (s, 1H, NH) 7.96 (d, 1H, J=8.25 Hz, NH), 8.12 (d, 1H, J=7.4 Hz, NH), 10.75 (s. 1H, 4-H), 12.0 (s, broad, 1H, COOH) ppm.

Analysis for C$_{18}$H$_{22}$N$_4$O$_7$.0.4H$_2$O (413.60): calc.: 52.27% C 5.56% H 13.55% N found: 52.76% C 5.68% H 13.06% N

EXAMPLE 51

(2S)-(+)-N-(3,4-Dihydro-2-methyl-3-oxo-2H-1,4-benzoxazine-2-carbonyl)-L-alanyl-D-isoglutamine The compound was prepared from (2S)-(+)-benzyl-N-(3, 4-dihydro-2-methyl-3-oxo-2H-1,4-benzoxazine-2-carbonyl)-L-alanyl-D-isoglutaminate according to the procedure described in Example 27. The title product was in the form of a white foam, which was converted to, the crystalline form by reprecipitation from anhydrous ether. The compound had no sharp melting point.

Yield: 92%

Specific rotation: [α]$^{20}_D$=+17.9° (c=1.25, THF)

IR (KBr): ν=3600–3150, 3000–2500, 1702, 1501, 1449, 1381, 1229, 1175, 1132, 1052, 956, 757 cm$^{-1}$.

$^1$H-NMR (300 MHz, DMSO-d$_6$): δ=1.22 (d, 3H, J=6.9 Hz, CH$_3$-Ala), 1.62 (s, 3H, CH$_3$), 1.65–1.80 (m, 1H, CH$_2$-βiGln), 1.85–2.05 (m, 1H, CH$_2$βiGln), 2.16 (t, 2H, CH$_2$γiGln), 4.10–4.22 (m, 2H, CH-Ala, CH-iGln), 6.85–7.02 (m, 3H, 3H-arom.), 7.05 (m, 1H, 1H-arom.), 7.16 (s, 1H, NH), 7.28 (s, 1H, NH), 7.65 (d, 1H, J=8.25 Hz, NH), 8.20 (d, 1H, J=7.4 Hz, NH), 10.90 (s, 1H, 4-H), 12.0 (s, broad, 1H, COOH) ppm.

Analysis for C$_{18}$H$_{22}$N$^7$ O$_7$ (406.39): calc.: 53.20% C 5.46% H 13.79% N found: 53.27% C 5.67% H 13.51% N

EXAMPLE 52

(2R)-(+)-Benzyl-N-(3,4-dihydro-2,4-dimethyl-3-oxo-2H-1,4-benzoxazine-2-carbonyl)-L-alanyl-D-isoglutaminate The compound was prepared from (S)-(+)-3,4-dihydro-2, 4-dimethyl-3-oxo-2H-1,4-benzoxazine-2-carboxylic acid according to the procedure described in Example 26. The title product was in the form of a white foam, which was purified by column chromatography (silica gel; dichloromethane/methanol=20:1) and converted to the crystalline form by reprecipitation from anhydrous ether. The compound had no sharp melting point.

Yield: 73%

Specific rotation: $[\alpha]^{20}_D$=+20.1° (c=0.5, methanol) +33.2° (c=0.31, THF)

IR (KBr): ν=3260, 3082, 2920, 1715, 1631, 1567, 1442, 1330, 1219, 1119, 897 cm$^{-1}$.

$^1$H-NMR (300 MHz, DMSO-d$_6$): δ=1.01 (d, 3H, J=7.09 Hz, CH$_3$-Ala), 1.68 (s, 3H, CH$_3$), 1.70–1.83 (m, 1H, CH$_2$-βiGln), 1.95–2.07 (m, 1H, CH$_2$-βiGln), 2.30–2.35 (m, 2H, CH$_2$-γiGln), 3.29 (s, 3H, N—CH$_3$), 4.0–4.24 (m, 2H, CH-Ala, CH-iGln), 5.07 (s, 2H, CH$_2$-benzyl), 7.01–7.17 (m, 5H, 4H-arom., NH), 7.32–7.38 (m, 6H, 5H-arom. (benzyl), NH), 7.96 (d, 1H, J=8.25 Hz, NH), 8.20 (d, 1H, J=7.38 Hz, NH) ppm.

Analysis for C$_{26}$H$_{30}$N$_4$O$_7$ (510.55): calc.: 61.17% C 5.92% H 10.97% N found: 60.89% C 6.00% H 10.99% N

EXAMPLE 53

(2S)-(−)-Benzyl-N-(3,4-dihydro-2,4-dimethyl-3-oxo-2H-1,4-benzoxazine-2-carbonyl)-L-alanyl-D-isoglutaminate The compound was prepared from (R)-(−)-3,4-dihydro-2,4-dimethyl-3-oxo-2H-1,4-benzoxazine-2-carboxylic acid according to the procedure described in Example 26. The title product was in the form of a white foam, which was purified by column chromatography (silica gel; dichloromethane/methanol=20:1) and converted to the crystalline form by reprecipitation from anhydrous ether. The compound had no sharp melting point.

Yield: 59%

Specific rotation: $[\alpha]^{20}_D$=−2.7° (c=0.5, methanol) −13.2° (c=0.38, THF)

IR (KBr): ν=3263, 3080, 2925, 1715, 1631, 1567, 1444, 1329, 1219, 1121, 896 cm$^{-1}$.

$^1$H-NMR (300 MHz, DMSO-d$_6$): δ=1.20 (d, 3H, J=7.09 Hz, CH$_3$-Ala), 1.61 (s, 3H, CH$_3$), 1.65–1.77 (m, 1H, CH$_2$-βiGln), 1.92–2.03 (m, 1H, CH$_2$-βiGln), 2.27–2.33 (m, 2H, CH$_2$-γiGln), 3.28 (s, 3H, N—CH$_3$), 4.13–4.24 (m, 2H, CH-Ala, CH-iGln), 5.08 (s, 2H, CH$_2$-benzyl), 6.99–7.15 (m, 5H, 4H-arom., NH), 7.30–7.39 (m, 6H, 5H-arom. (benzyl), NH), 7.57 (d, 1H, J=8.25 Hz, NH), 8.27 (d, 1H, J=7.62 Hz, NH) ppm.

Analysis for C$_{26}$H$_{30}$ N$_4$O$_7$ (510.55): calc.: 61.17% C 5.92% H 10.97% N found: 60.95% C 5.77% H 11.32% N

EXAMPLE 54

(2R)-(+)-N-(3,4-Dihydro-2,4-dimethyl-3-oxo-2H-1,4-benzoxazine-2-carbonyl)-L-alanyl-D-isoglutamine The compound was prepared from (2R)-(+)-benzyl-N-(3,4-dihydro-2,4-dimethyl-3-oxo-2H-1,4-benzoxazine-2-carbonyl)-L-alanyl-D-isoglutaminate according to the procedure described in Example 27. The title product was in the form of a white foam, which was converted to the crystalline form by reprecipitation from anhydrous ether. The compound had no sharp melting point.

Yield: 92%

Specific rotation: $[\alpha]^{20}_D$=+33.10° (c=0.5, methanol) +44.5° (c=0.13, THF)

IR (KBr): ν=3620–3150, 1692, 1654, 1502, 1387, 1239, 1141 cm$^{-1}$.

$^1$H-NMR (300 MHz, DMSO-d$_6$): δ=0.92 (d, 3H, J=6.9 Hz, CH$_3$-Ala), 1.59 (s, 3H, CH$_3$), 1.64–1.69 (m, 1H, CH$_2$-βiGln), 1.78–1.88 (m, 1H, CH$_2$-βiGln), 2.04–2.10 (m, 2H, CH$_2$-γiGln), 3.19 (s, 3H, N—CH$_3$), 3.97–4.12 (m, 2H, CH-Ala, CH-iGln), 6.93–7.08 (m, 5H, 4H-arom., NH), 7.24 (s, 1H, NH), 7.85 (d, 1H, J=8.25 Hz, NH), 8.09 (d, 1H, J=7.38 Hz, NH), 12.04 (s, broad, 1H, COOH) ppm.

Analysis for C$_{19}$H$_{24}$N$_4$O$_7$.H$_2$O (438.435): calc.: 52.05% C 5.98% H 12.78% N found: 52.23% C 6.07% H 12.55% N

EXAMPLE 55

(2S)-(−)-N-(3,4Dihydro-2,4dimethyl-3-oxo-2H-1,4-benzoxazine-2-carbonyl)-L-alanyl-D-isoglutamine The compound was prepared from (2S)-(−)-benzyl-N-(3,4-dihydro-2,4dimethyl-3-oxo-2H-1,4benzoxazine-2-carbonyl)-L-alanyl-D-isoglutaminate according to the procedure described in Example 27. The title product was in the form of a white foam, which was converted to the crystalline form by reprecipitation from anhydrous ether. The compound had no sharp melting point.

Yield: 97%

Specific rotation: $[\alpha]^{20}_D$=−10.0° (c=0.5, methanol)

IR (KBr): ν=3679–3154, 1690, 1654, 1506, 1388, 1240, 1140 cm$^{-1}$.

$^1$H-NMR (300 MHz, DMSO-d$_6$): δ=1.20 (d, 3H, J=7.08 Hz, CH$_3$-Ala), 1.63 (s, 3H, CH$_3$), 1.65–1.78 (m, 1H, CH$_2$-βiGln), 1.84–1.96 (m, 1H, CH$_2$-βiGln), 2.13–2.18(m 2H, CH$_2$-γiGln), 3.30 (s, 3H, N—CH$_3$), 4.10–4.24 (m, 2H, CH-Ala, CH-iGln), 7.01–7.18 (m, 5H, 4H-arom., NH), 7.27 (s, 1H, NH), 7.59 (d, 1H, J=8.31 Hz, NH), 8.24 Hz, NH), 8.24 (d, 1H, J=7.57 Hz, NH), 12.10 (s, broad, 1H, COOH) ppm.

Analysis for C$_{19}$H$_{24}$N$_4$O$_7$.H$_2$O (438.435): calc.: 52.05% C 5.98% H 12.78% N found: 52.40% C 6.31% H 12.02% N.

PHARMACEUTICAL PREPARATIONS

The pharmaceutical preparations of the invention can be in the form of coated pills, tablets, capsules, ampoules or aerosols to be used on mucuous membranes. Preparations suitable for parenteral application can also contain liposomes.

The pharmaceutical preparations of the invention comprise the pharmacologically active compound alone or together with a pharmaceutically acceptable carrier chosen with respect to the mode of application. Pharmaceutical preparations are manufactured according to methods known per se.

The dose, the frequency and the mode of application will depend on various factors such as the intended use (e.g. for the prevention against the side effects after cancer chemotherapy, the treatment of primary and secondary immunodeficiency or of various types of infections and for the non-specific cancer therapy) and the patient's condition.

A suitable dose for an adult will be from 0.02 to 100 mg/day. The exact dose, the frequency and the mode of application will be chosen with respect to other factors than can affect the effect of the drug such as the patient's age, weight, sex, type and severity of his condition and his response to the medication.

EXAMPLE

| Lyophilized injections | |
|---|---|
| Compound 1 | 1 mg |
| Manitol | 45 mg |
| NaOH or HCl for pH adjustment | q.s. |
| Water for injections | 1 ml |

BIOLOGICAL TESTS

The compounds of the present invention cause therapeutically significant effects upon immunologically based systems. Thus they can be considered as potential medicaments for the prevention and therapy of side effects after cancer chemotherapy, for the therapy of chronic and recurrent infections due to impaired immunity as well as for non-specific cancer therapy.

Immunorestoration Test

The test substance or a vehicle was administered i.p. to groups of 10 mice on days 1, 3 and 5 of the experiment in four different doses (0.1, 1, 10 and 100 mg/kg). Cyclophosphamide (30 mg/kg) was administered p.o. on days 2, 4, and 6. One day after the last immunosuppressant (cyclophosphamide) dose, the mice were challenged with a suspension of *Candida albicans* sufficient to result in the mortality of a predominant number of the animals.

| Substance | Mode | Dose (mg/kg) | Number of survivals | Note |
|---|---|---|---|---|
| Control distilled water | i.p. | | 9 | n = 10 |
| Cyclophosphamide | p.o. | 30 × 3 | 3 | n = 10 |
| Compound 1*** | i.p. | 100 × 3 | 6 | n = 10 |
| + cyclophosphamide | i.p | 10 × 3 | 7 | n = 10 |
| | i.p. | 1 × 3 | 6 | n = 10 |
| | i.p. | 0.1 × 3 | 6 | n = 10 |
| U.S. 5,231,216** | i.p. | 100 × 3 | 6 | n = 10 |
| + cyclophosphamide | i.p | 10 × 3 | 6 | n = 10 |
| | i.p. | 1 × 3 | 5 | n = 10 |
| | i.p. | 0.1 × 3 | 2 | n = 10 |
| Romurtide (Nopia ®) + cyclophosphamide | i.p. | 0.1* × 3 | 5 | n = 10 |

*half of the human dose
***Compound 1 is: N-[trans-2-(2'-dodecanoylaminocyclohexyloxy)acetyl]-L-alanyl-D-isoglutamine, which was tested as an equimolar mixture (1:1) of both possible diastereomers.
***Compound 1: N-(3,4-dihydro-2,4-dimethyl-3-oxo-2H-1,4-benzoxazine-2-carbonyl)-L-alanyl-D-isoglutamine A greater than 30% survival caused by any of the tested compounds is considered as a consequence of immunorestoration.

The immunorestoration test showed that by the compound 1 of the present invention the immunorestorative effect can be achieved already at a dose that is up to 100 times lower in comparison with the related compounds described in U.S. Pat. No. 5,231,216. The activity of compound 1 is also superior to that of the MDP analogue romurtide, which is used as an immunostimulant (Drugs of the Future 15, 538, 1990) for the treatment of leukopenia resulting from the chemotherapy of cancerous diseases; evidently, a typical immunorestorative effect is in question.

Determination of haemolytic plaques for the assessment of the maturation of lymphocytes B A suspension of sheep erythrocytes (Institute of Microbiology, Faculty of Medicine, Ljubljana, Slovenia) in physiological saline ($10^8$/ml) was used for the immunization. First, individual mice were administered 0.2 ml of this suspension by i.p. injection, followed next day by 0.1 ml (1 μg/mouse) of the test substance. Romurtide was dissolved in a solution of D-manitol (45 mg/ml; Nopia) and compound 1 was dissolved in physiological saline. The immunization was completed on day 5 after the administration of sheep erythrocytes and the mice were sacrificed.

Their spleens were removed and homogenized in Gibco 199 medium. The lymphocytes were separated on the Ficol separating medium (Pharmacia, Uppsala, Sweden). After repeated rinsing with Gibco 199 medium, the cells were resuspended in RPMI 1640 nutrient medium with added 10% of foetal calf serum and streptomycin. To 50 μl of the cell suspension, 450 μl of trypan blue were added and the cells were counted in Neubauer's chamber. The number of lymphocytes per ml of the cell suspension was calculated. To 100 μl of the diluted cell suspension, there were added 200 μl of the RPMI 1640 nutrient medium, 50 μl of a 10% suspension of sheep erythrocytes and 50 μl of guinea pig complement (Institute for Microbiology, Faculty of Medicine, Ljubljana, Slovenia). The reaction mixture (RM) was put into the prepared chambers on the slide, the chambers were sealed with white wax and incubated at 37° C. for 60 minutes. After the completion of the incubation, the plaques were counted under microscope.

The number of plaques per $1 \times 10^6$ cells was calculated according to the following equations:

$$\text{Number of plaques} = \frac{1 \times 10^6 \times \text{number plaques per chamber}}{\text{A cells per chamber}}$$

A cells per chamber =

$$\frac{\text{amount of } RM \text{ per chamber}(\mu 1) \times \text{number of cells in } RM}{\text{amount of } RM(\mu 1)}$$

In the table, the values are presented as stimulation indexes (number of plaques in the test group/number of plaques in the control group).

| | Stimulation index | | |
|---|---|---|---|
| Dose μ/mouse | A Compound 1 | B Nopia | P* A:B |
| | x ± s.e.m.; n = 5 | | |
| 1 | 3.64 ±0.20 | 1.06 ±0.03 | <0.001 |
| 10 | 5.32 ±0.53 | 1.92 ±0.13 | <0.001 |

*Student's test for the comparison of stimulation indexes

Antitumor activity

Solid subcutaneous B-16 melanoma were used on C57B1/6 strain mice of 8 to 10 weeks.

The tumors were implanted by injection of $3 \times 10^5$ live tumor cells into the left lower abdomen of mice. The suspension of tumor cells was prepared in ENAM (Eagle's Minimal Essential Medium, Sigma Chemical Co., St. Louis, Mo., U.S.A.) enriched with 2% foetal calf serum (FCS, Sigma). Tumor cells (B-16 melanoma tumor cells, clone F1, ATCC, Rockville, Md.) for implantation into test animals were grown in vitro in a cell culture.

The application of the test substances was started 24 hours after the tumor induction. The test substance was injected five times on five consecutive days in a dose of 10 mg/kg, the dose of Nopia was 1 mg/kg of test animals daily (a fivefold human dose).

The antitumor activity of the active compounds was monitored by recording the tumor emergence, daily measuring the tumor diameters and calculating the tumour volumes.

Surprisingly, it was found that in some animals treated with compounds 2*, 3* and 4*, the healing of tumors took place. So e.g. in one of nine animals treated with the compound 4* and in two of eight animals treated with the compound 2*, a complete regression of tumors took place. In the tumors that underwent the regression, the growth stopped 10–11 days after implantation of tumor cells to disappear completely in the following 1 or 2 days. On day 20 after the tumor induction, these animals were still without tumors.

Similar observations were made in animals treated with the compound 3*. Between days 9 and 12, a regression of the tumors set in with some animals. On day 20 after the tumor induction, three animals of nine were still without tumors. These results indicate that the compounds of the present invention are capable of stimulating the immune system and indirectly affect the tumor growth.

The growth of tumors that upon administration of the tested active compounds did not disappear is shown in FIG. 1. These tumors also showed a tendency to the retardation of growth.

Compound 2: (2R)-N-(3,4-dihydro-2-methyl-3-oxo-2H-1,4-benzoxazine-2-carbonyl)-L-alanyl-D-isoglutamine Compound 3: N-(3,4-dihydro-2-methyl-3-oxo-2H-1,4-benzoxazine-2-carbonyl)-L-alanyl-D-isoglutamine Compound 4: (2S)-N-(3,4-dihydro-2,4-dimethyl-3-oxo-2H-1,4-benzoxazine-2-carbonyl)-L-alanyl-D-isoglutamine

Pyrogenous activity

Figure 1:
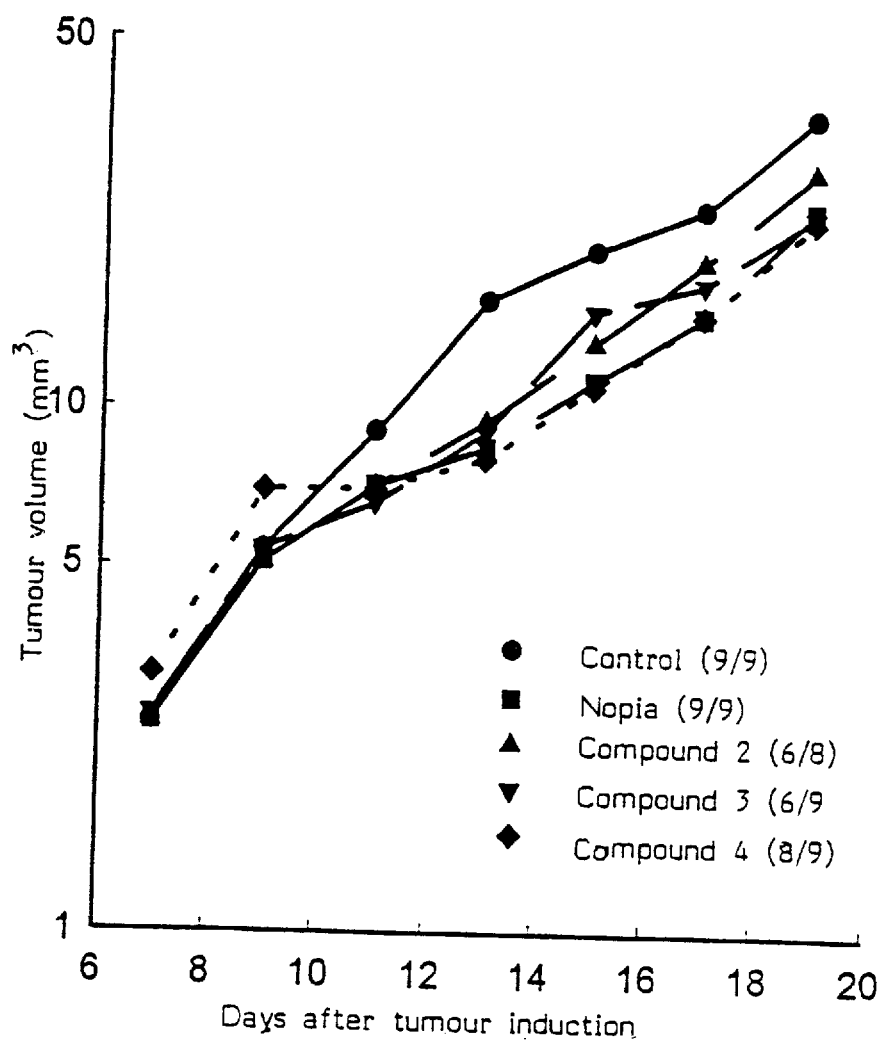
FIG. 1 shows the effect of compounds 2, 3, 4 and Nopia, respectively, on the growth of solid subcutaneous B-16 tumors in which no regression took place (number of animals having tumors on day 20/number of animals having tumors on day 7). The test animals were treated for five consecutive days by intraperitoneal injections of the active compounds and control, respectively. The treatment was started 24 hours after tumor induction.

The pyrogenous activity was determined according to the method of USPXXII. In constrast to MDP, the compound 1 did not show any pyrogenous activity.

Toxicity

The average lethal dose ($LD_{50}$) of the compound 1 in male mice was >250 mg/kg at intravenous application.

We claim:

1. Heterocyclic acyldipeptides of the formula I

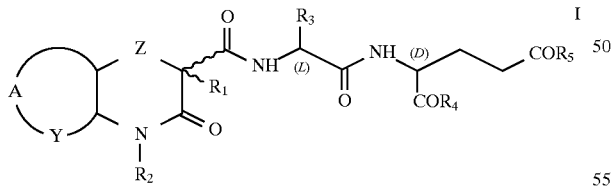

wherein

Z represents an oxygen or sulphur atom or a —$CH_2$— group;

$R_1$ represents hydrogen, a straight or branched chain 1–4C alkyl, trifluoromethyl or benzyl group;

$R_2$ represents hydrogen, a straight or branched chain 1–4C alkyl or benzyl group;

$R_3$ represents hydrogen, a straight or branched chain 1–12C alkyl or trifluoromethyl group;

$R_4$ and $R_5$, which are identical or different, represent an $OR_6$ or $NHR_6$ group, wherein $R_6$ is hydrogen, a straight or branched chain 1–18C alkyl or benzyl group;

Y represents a —$CH_2$—, =CH— or =N— group;

A represents a —$(CH_2)_3$— group when Y is —$CH_2$—, wherein fusion of the Z containing ring with the A containing ring being trans, or a

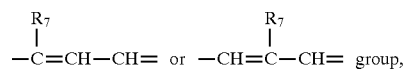

wherein $R_7$ represents H, F, Br, Cl, a straight or branched chain 1–4C alkyl, 1–4C alkoxy, trifluoromethyl, nitro, amino, alkylamino or dialkylamino group, when Y is =CH— or =N—;

and optical diastereomers thereof and their pharmaceutically acceptable salts.

2. The acyldipeptides of claim 1 being N-(3,4-Dihydro-2,4-dimethyl-3-oxo-2H-1,4-benzoxazine-2-carbonyl)-L-alanyl-D-isoglutamine.

3. The acyldipeptides of claim 1 being (2S)-N-(3,4-Dihydro-2,4-dimethyl-3-oxo-2H-1,4-benzoxazine-2-carbonyl)-L-alanyl-D-isoglutamine.

4. The acyldipeptides of claim 1 being (2R)-N-(3,4-Dihydro-2-methyl-3-oxo-2H-1,4-benzoxazine-2-carbonyl)-L-alanyl-D-isoglutamine.

5. The acyldipeptides of claim 1 being N-(3,4-Dihydro-2-methyl-3-oxo-2H-1,4-benzoxazine-2-carbonyl)-L-alanyl-D-isoglutamine.

6. Heterocyclic acylpeptides of formula I according to claim 1 having R or S absolute configuration at carbon atom bearing R1 and their pharmaceutically acceptable salts.

7. A process for the preparation of heterocyclic acyl dipeptides of the formula I

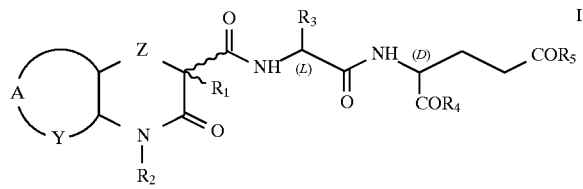

wherein

Z represents an oxygen or sulphur atom or a —$CH_2$— group;

$R_1$ represents hydrogen, a straight or branched chain 1–4C alkyl trifluoromethyl or benzyl group;

$R_2$ represents hydrogen, a straight or branched chain 1–4C alkyl, or benzyl group;

$R_3$ represents hydrogen, a straight or branched chain 1–12C alkyl or trifluoromethyl group;

$R_4$ and $R_5$, which are identical or different, represent an $OR_6$ or $NHR_6$ group, wherein $R_6$ is hydrogen, a straight or branched chain 1–18C alkyl or benzyl group;

Y represents a —$CH_2$—, =CH— or =N— group;

A represents a —$(CH_2)_3$— group when Y is —$CH_2$—, wherein fusion of the Z containing ring with the A containing ring being trans, or a

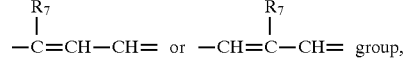

wherein $R_7$ represents H, F, Br, Cl, a straight or branched chain 1–4C alkyl, 1–4C alkoxy, trifluoromethyl, nitro, amino, alkylamino or dialkylamino group, when Y is =CH— or =N—;
wherein heterocyclic carboxylic acids or their enantiomers of formula II

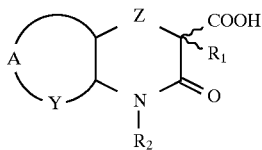

wherein
Z represents an oxygen or sulphur atom or a —CH$_2$— group;
R$_1$ represents hydrogen, a straight or branched chain 1–4C alkyl trifluoromethyl or benzyl group;
R$_2$ represents hydrogen, a straight or branched chain 1–4C alkyl, or benzyl group;
Y represents a —CH$_2$—, =CH— or =N— group;
A represents a —(CH$_2$)$_3$— group when Y is —CH$_2$—, wherein fusion of the Z containing ring with the A containing ring being trans, or a

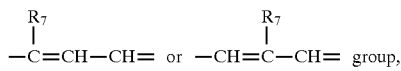

wherein R$_7$ represents H, F, Br, Cl, a straight or branched chain 1–4C alkyl, 1–4C alkoxy, trifluoromethyl, nitro, amino, alkylamino or dialkylamino group, when Y is =CH— or =N—;
are reacted with dipeptides of formula III

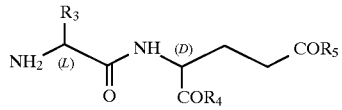

wherein
R$_3$ represents hydrogen, a straight or branched chain 1–12C alkyl or trifluoromethyl group;
R$_4$ and R$_5$ which are identical or different, represent an OR$_6$ or NHR$_6$ group, wherein
R$_6$ is hydrogen, a straight or branched chain 1–18C alkyl or benzyl group; in polar aprotic solvents, at temperatures from −10° to 25° C., using common reagents for the formation of the peptide bond and removing the protecting group(s) by hydrogenation using Pd/C as the catalyst.

8. Pharmaceutical preparations, comprising a therapeutically effective amount of heterocyclic acyldipeptides according to claims 1 as the active ingredient together with common pharmaceutically acceptable carriers and adjuvants.

9. Pharmaceutical preparations, comprising a therapeutically effective amount of heterocyclic acyldipeptides according to claim 2 as the active ingredient together with common pharmaceutically acceptable carriers and adjuvants.

10. Pharmaceutical preparation comprising therapeutically effective amount of the heterocyclic acyldipeptide according to claim 2 as the active ingredient together with common pharmaceutically acceptable carriers and adjuvants.

11. Pharmaceutical preparation comprising therapeutically effective amount of the heterocyclic acyldipeptide according to claim 3 as the active ingredient together with common pharmaceutically acceptable carriers and adjuvants.

12. Pharmaceutical preparation comprising therapeutically effective amount of the heterocyclic acyldipeptide according to claim 4 as the active ingredient together with common pharmaceutically acceptable carriers and adjuvants.

13. Pharmaceutical preparation comprising therapeutically effective amount of the heterocyclic acyldipeptide according to claim 5 as the active ingredient together with common pharmaceutically acceptable carriers and adjuvants.

14. A method for treating a patient suffering from melanoma which comprises administering to said patient a therapeutically effective amount of a pharmaceutical composition containing a heterocyclic acyldipeptide of claim 1.

15. A method for treating a patient suffering from melanoma which comprises administering to said patient a therapeutically effective amount of a pharmaceutical composition containing a heterocyclic acyldipeptide of claim 2.

16. A method for treating immunosuppressive side effects due to chemotherapeutic agents useful in neoplastic disease selected from the group consisting of alkylating agents and antimetabolites, which comprises administering to a patient in need thereof a therapeutically effective amount of a pharmaceutical composition containing a heterocyclic acyldipeptide of claim 1.

17. A method for treating immunosuppressive side effects due to chemotherapeutic agents useful in neoplastic disease selected from the group consisting of alkylating agents and antimetabolites, which comprises administering to a patients in need thereof a therapeutically effective amount of a pharmaceutical composition containing a heterocyclic acyldipeptide of claim 2.

18. A method for treating opportunistic infections in an immunocompromised patient comprising administering to said patient a therapeutically effective amount of a pharmaceutical composition containing a heterocyclic acyldipeptide of claim 1.

19. A method for treating opportunistic infections in an immunocompromised patient comprising administering to said patient a therapeutically effective amount of a pharmaceutical composition containing a heterocyclic acyldipeptide of claim 2.

* * * * *